United States Patent
Wilson et al.

(10) Patent No.: US 6,355,435 B1
(45) Date of Patent: Mar. 12, 2002

(54) METHODS FOR DETECTING AND ENUMERATING *CAMPYLOBACTER JEJUNI* IN ENVIRONMENTAL SAMPLES AND FOR IDENTIFYING ANTIBIOTIC-RESISTANT STRAINS

(75) Inventors: David L. Wilson, Grand Ledge; John E. Linz; John B. Kaneene, both of East Lansing; Linda S. Mansfield, Bath, all of MI (US); Robert D. Walker, Laurel, MD (US); Thomas C. Newman, Haslett, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/656,286

(22) Filed: Sep. 6, 2000

Related U.S. Application Data

(60) Provisional application No. 60/153,415, filed on Sep. 10, 1999, and provisional application No. 60/153,417, filed on Sep. 10, 1999.

(51) Int. Cl.[7] .............. C12Q 1/68; C12P 19/34; C07H 21/02; C07H 21/04
(52) U.S. Cl. ............... 435/6; 435/91.2; 435/800; 536/23.1; 536/24.31; 536/24.33
(58) Field of Search .................. 435/6, 91.2, 800; 536/23.1, 24.31, 24.33

(56) References Cited

U.S. PATENT DOCUMENTS

| | | | | |
|---|---|---|---|---|
| 5,645,994 A | * | 7/1997 | Huang ........................ | 435/6 |
| 5,716,784 A | | 2/1998 | Di Cesare ................... | 435/6 |
| 5,866,336 A | | 2/1999 | Nazarenko et al. ......... | 435/6 |
| 5,972,721 A | * | 10/1999 | Bruno et al. ............... | 435/526 |
| 6,015,670 A | * | 1/2000 | Goodfellow ................ | 435/6 |

OTHER PUBLICATIONS

GenEmbl Accession No.: 151844, Oct. 7, 1997.*
Hughs et al., J. Infect. Dis. 176 (Suppl. 2): S92–S98 (1997).
Blaser, J. Infect. Dis. 176 (Suppl.): S103–S105 (1997).
Altkreuse et al., Emerg. Infect. Dis. 5: 28–35 (1999).
Gaudreau et al., Antimicrob. Agents Chemother. 42: 2106–2108 (1998).
Gaunt et al., J. ANtimicrob. Chemother. 37: 747–757 (1996).
Moore et al., Vet. Rec. 138: 306–307 (1996).
Lee et al., Internat. J. Food Microbiol. 24: 161–170 (1994).
Taylor et al., Antimicrob. Agents Chemother. 32: 1107–1112 (1988).
Tenover et al., Antimicrob. Agents Chemother. 27: 37–41 (1985).
Wang et al., Antimicrob. Agents Chemother. 37: 457–463 (1993).
Charvalos et al., J. Clin. Lab. Anal. 10: 129–133 (1996).
Husmann et al., J. Clin. Microbiol. 35: 2398–2400 (1997).
Gibreel et al., Antimicrob. Agents Chemother. 42: 3276–3278 (1998).
Ruiz et al., Microbiol. Immunol. 42: 223–226 (1998).
Heid et al., Genome Res. 6: 986–994 (1996).
Ausubel et al., In Current Protocols in Molecular Biology. John Wiley & Sons, Inc. New York, NY.
Waegel and Nachamkin, Molec. and Cell. Probes 10: 75–80 (1996).

* cited by examiner

*Primary Examiner*—Kenneth R. Horlick
*Assistant Examiner*—Alexander H. Spiegler
(74) *Attorney, Agent, or Firm*—Ian C. McLeod

(57) ABSTRACT

The present invention provides a process for detecting and enumerating *Campylobacter jejuni* in an environmental sample. The present invention further provides a process which can distinguish antibiotic resistant strains of *Campylobacter jejuni* from wild-type strains, in particular, antibiotic-resistant strains resistant to high levels of ciprofloxacin. Both processes use PCR primers which flank a target sequence unique to *Campylobacter jejuni* in combination with one or more dual-labeled oligonucleotide probes complementary to the target sequence wherein the dual-labeled probes enable detection of PCR amplification by fluorescence detection means.

29 Claims, 14 Drawing Sheets

```
                              JL 238
              1                                                        50
    cj33291   TTTTGTCAAA  TCAGCCCGTA  TAGTGGGTGC  TGTTATAGGT  CGTTATCACC
    cj33560   TTTTGTCAAA  TCAGCCCGTA  TAGTGGGTGC  TGTTATAGGT  CGTTATCACC
 cj33560cr6   TTTTGTCAAA  TCAGCCCGTA  TAGTGGGTGC  TGTTATAGGT  CGTTATCACC
    cj33292   TTTTGTCAAA  TCAGCCCGTA  TAGTGGGTGC  TGTTATAGGT  CGTTATCATC
 cj33292cr216 TTTTGTCAAA  TCAGCCCGTA  TAGTGGGTGC  TGTTATAGGT  CGTTATCATC
    cj49349   TTTTGTTAAA  TCAGCCCGTA  TAGTGGGTGC  TGTTATAGGT  CGTTATCACC
   ccl777708  ATATAAAAAA  TCTGCTCGTA  TAGTAGGGGA  TGTTATCGGT  AAGTATCATC
    cc43473   ATATAAAAAA  TCTGCTCGTA  TAGTAGGGGA  TGTTATCGGT  AAGTATCATC
    cl43675   ATATAAAAAA  TCAGCTCGTA  TAGTAGGGGA  TGTTATAGGT  AAGTATCATC
    cf27374   ATATAAAAAG  TCTGCTCGTA  TAGTAGGTGA  TGTTATCGGT  AAGTATCACC 51         TAQ2&TAQ3                                    100
    cj33291   CACATGGAGA  TACAGCAGTT  TATGATGCTT  TGGTTAGAAT  GGCTCAAGAT
    cj33560   CACATGGAGA  TACAGCAGTT  TATGATGCTT  TGGTTAGAAT  GGCTCAAGAT
 cj33560cr6   CACATGGAGA  TATAGCAGTT  TATGATGCTT  TGGTTAGAAT  GGCTCAAGAT
    cj33292   CACATGGAGA  TACAGCAGTT  TATGATGCTT  TGGTTAGAAT  GGCTCAAGAT
 cj33292cr216 CACATGGAGA  TATAGCAGTT  TATGATGCTT  TGGTTAGAAT  GGCTCAAGAT
    cj49349   CGCATGGAGA  TACAGCAGTT  TATGATGCTT  TAGTTAGAAT  GGCTCAAGAT
   ccl777708  CACATGGCGA  TACTGCTGTT  TACGATGCCT  TAGTAAGAAT  GGCACAAGAT
    cc43473   CACATGGCGA  TACTGCTGTT  TACGATGCCT  TAGTAAGAAT  GGCACAAGAT
    cl43675   CGCATGGTGA  TGTTGCTGTA  TATGATGCTT  TGGTTAGAAT  GGCACAAGAT
    cf27374   CGCACGGCGA  TACTGCGGTA  TATGACGCTT  TAGTTAGAAT  GGCTCAGAAC 101                                                     150
    cj33291   TTTTCTATGA  GATATCCAAG  TATTACAGGA  CAAGGCAACT  TTGGATCTAT
    cj33560   TTTTCTATGA  GATATCCAAG  TATTACAGGA  CAAGGCAACT  TTGGATCTAT
 cj33560cr6   TTTTCTATGA  GATATCCAAG  TATTACAGGA  CAAGGCAACT  TTGGATCTAT
    cj33292   TTTTCTATGA  GATATCCAAG  TATTACAGGA  CAAGGCAACT  TTGGATCTAT
 cj33292cr216 TTTTCTATGA  GATATCCAAG  TATTACAGGA  CAAGGCAACT  TTGGATCTAT
    cj49349   TTTTCTATGA  GATATCCAAG  TATTACAGGA  CAAGGTAACT  TTGGATCTAT
   ccl777708  TTCTCTATGC  GTTATCCAAG  TATCGATGGA  CAAGGAAACT  TTGGTTCTAT
    cc43473   TTCTCTATGC  GTTATCCAAG  TATCGATGGA  CAAGGAAACT  TTGGTTCTAT
    cl43675   TTTTCTATGC  GTTATCCAAG  TGTTGATGGA  CAAGGTAACT  TTGGCTCTAT
    cf27374   TTTTCTATGA  GAGTTCCTGC  AGTAGATGGT  CAAGGAAACT  TTGGCTCAGT
```

FIG. 3A

```
                 151                    TAQ1
     cj33291  AGATGGTGAT AGTGCCGCTG CGATGCGTTA TACTGAAGCA AAAATGAGTA
     cj33560  AGATGGTGAT AGTGCCGCTG CGATGCGTTA TACTGAAGCA AAAATGAGTA
  cj33560cr6  AGATGGTGAT AGTGCCGCTG CGATGCGTTA TACTGAAGCA AAAATGAGTA
     cj33292  AGATGGTGAT AGCGCTGCTG CGATGCGTTA TACTGAAGCA AAAATGAGTA
  cj33292cr216 AGATGGTGAT AGCGCTGCTG CGATGCGTTA TACTGAAGCA AAAATGAGTA
     cj49349  AGATGGCGAT AGTGCTGCTG CGATGCGTTA TACTGAAGCA AAAATGAGTA
    ccl777708 CGATGGTGAT GGCGCTGCTG CAATGCGTTA TACTGAAGCT AGAATGACAA
     cc43473  CGATGGTGAT GGCGCTGCTG CAATGCGTTA TACTGAAGCT AGAATGACAA
     cl43675  TGATGGGGAT GGCGCTGCTG CTATGCGTTA TACTGAGGCT AGAATGACTA
     cf27374  CGATGGCGAT GGCGCAGCCG CTATGCGTTA TACTGAAGCT AGAATGACGG 201      JL 239                                250
     cj33291  AACTTTCTCA TGAGCTTTTA AAAGATATAG ATAAAGATAC GGTCGATTTT
     cj33560  AACTTTCTCA TGAGCTTTTA AAAGATATAG ATAAAGATAC GGTCGATTTT
  cj33560cr6  AACTTTCTCA TGAGCTTTTA AAAGATATAG ATAAAGATAC GGTCGATTTT
     cj33292  AACTTTCTCA TGAGCTTTTA AAAGATATAG ATAAAGATAC GGTCGATTTT
  cj33292cr216 AACTTTCTCA TGAGCTTTTA AAAGATATAG ATAAAGATAC GGTCGATTTT
     cj49349  AACTTTCTCA TGAGCTTTTA AAAGATATAG ATAAAGATAC GGTCGATTTT
    ccl777708 TTTTAGCAGA AGAGCTTTTA CGCGATATAG ATAAAGATAC GGTCGATTTT
     cc43473  TTTTAGCAGA AGAGCTTTTA CGCGATATAG ATAAAGATAC GGTAGATTTT
     cl43675  TTTTAGCTGA AGAATTGTTG CGTGATATTG ATAAAGATAC GGTTGATTTT
     cf27374  TTTTGGCAGA GGAACTTTTA AGAGATTTAG ATAAAGATAC GGTTGATTTT 251                                           300
     cj33291  GTTCCAAATT ATGATGGTTC AGAAAGCGAA CCTGATGTTT TACCTTCTAG
     cj33560  GTTCCAAATT ATGATGGTTC AGAAAGCGAA CCTGATGTTT TACCTTCTAG
  cj33560cr6  GTTCCAAATT ATGATGGTTC AGAAAGCGAA CCTGATGTTT TACCTTCTAG
     cj33292  GTTCCAAATT ATGATGGTTC AGAAAGCGAA CCTGATGTTT TACCTTCTAG
  cj33292cr216 GTTCCAAATT ATGATGGTTC AGAAAGCGAA CCTGATGTTT TACCTTCTAG
     cj49349  GTTCCAAATT ATGATGGTTC AGAAAGCGAA CCTGATGTTT TACCTTCTAG
    ccl777708 GTTCCAAACT ACGATGATTC TATGAGTGAG CCCGATGTTT TACCTGCTAG
     cc43473  GTTCCAAACT ACGATGATTC TATGAGTGAG CCCGATGTTT TACCTGCTAG
     cl43675  GTACCAAATT ATGATGATTC TATGAGTGAG CCTGATGTTT TACCTGCTAG
     cf27374  ATACCAAATT ATGATGATAG TTTAAGCGAA CCAGATGTTT TACCCGCGCG
```

FIG. 3B

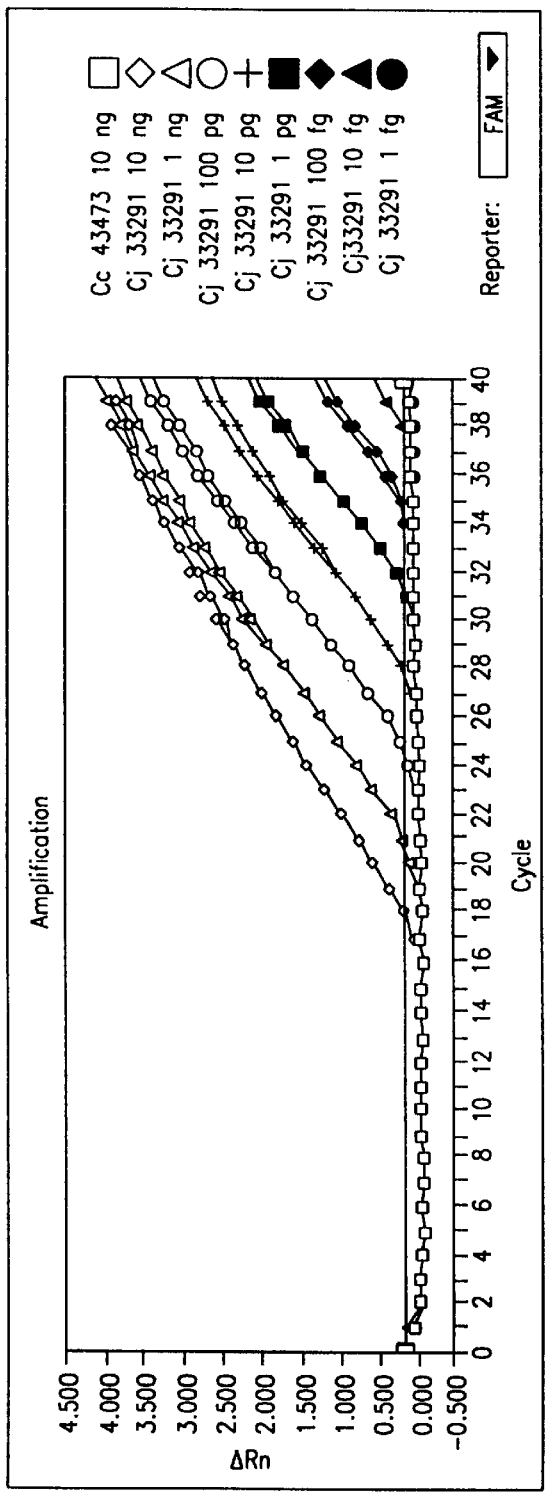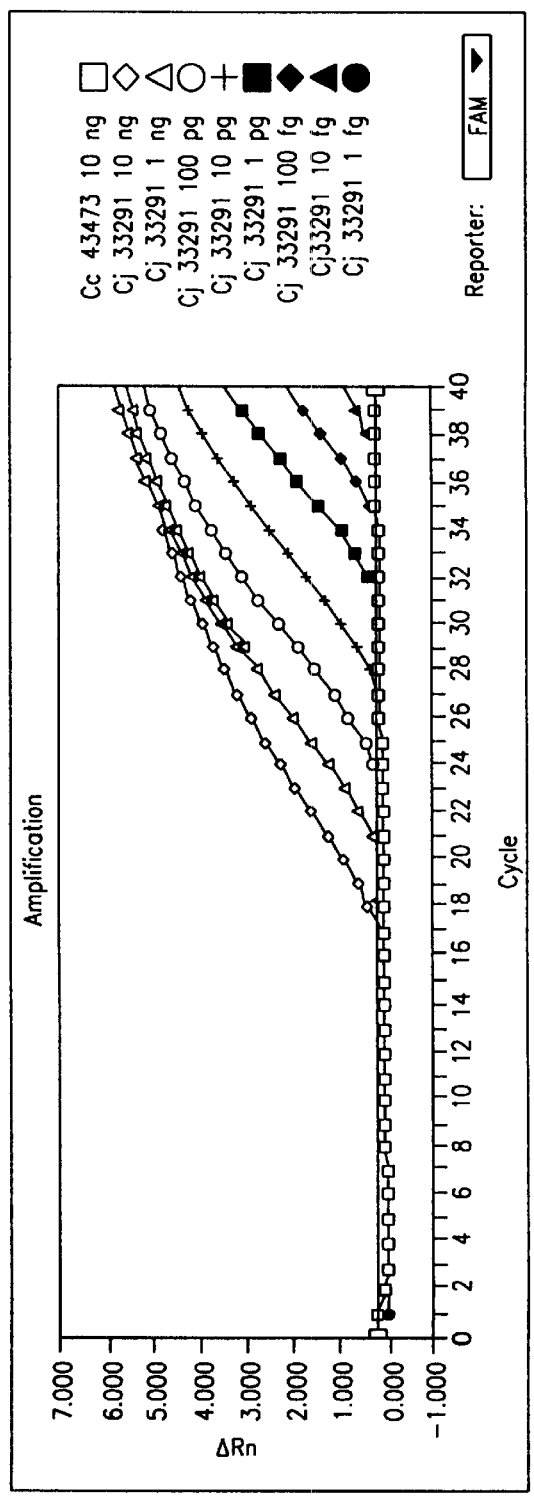

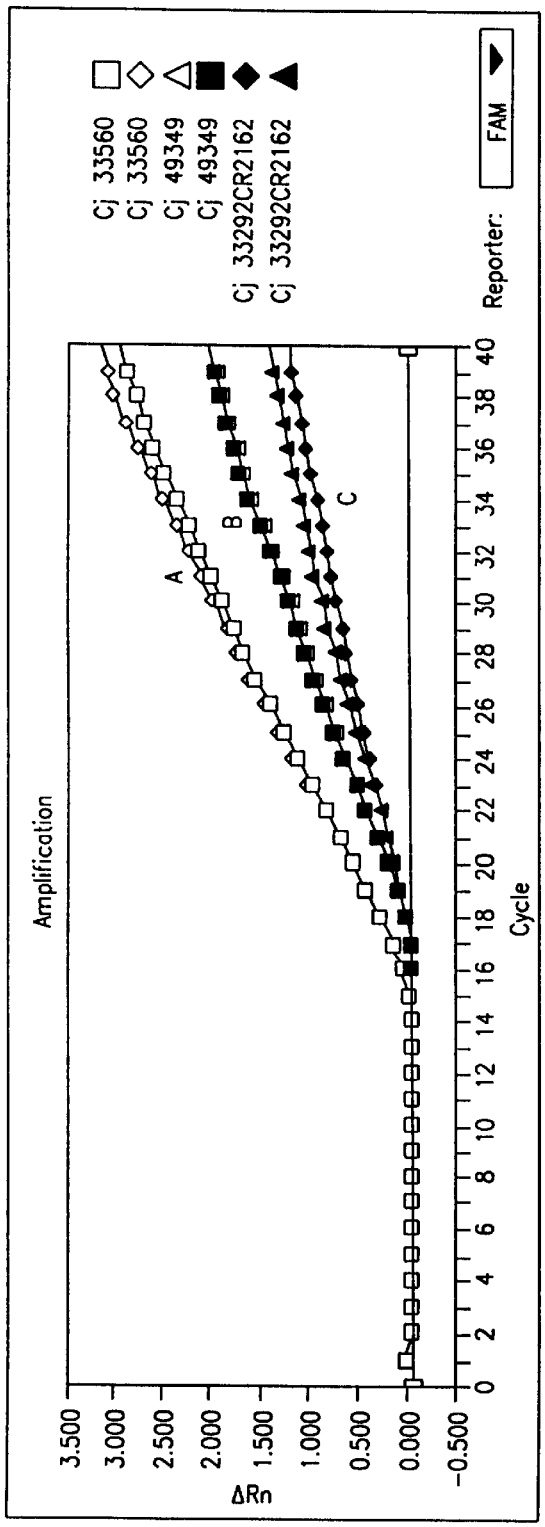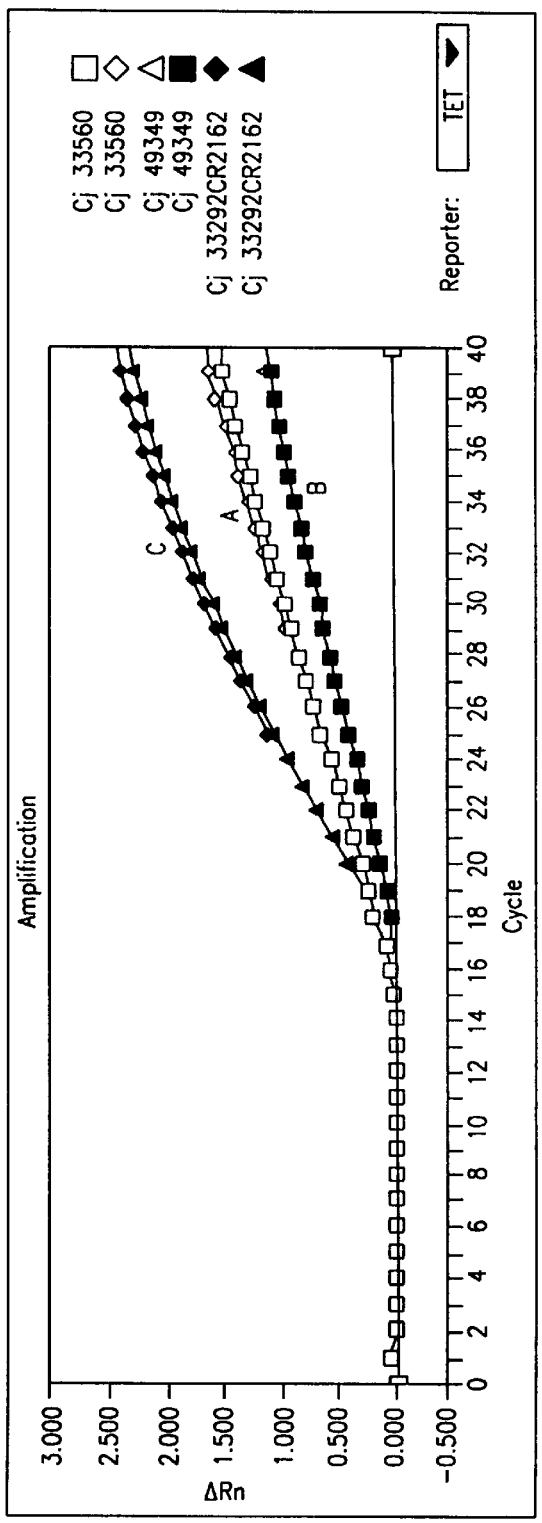

SEQUENCE LISTING

```
<160> NUMBER OF SEQ ID NOS:  19

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: PCR primer
      JL 297

<400> SEQUENCE: 1
ccatacctac ggcgataccg                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: PCR primer
      JL 299

<400> SEQUENCE: 2
gcctgaagcc ggtacaccgt                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: PCR primer
      JL 238

<400> SEQUENCE: 3
tgggtgctgt tataggtcgt                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR primer JL
      239

<400> SEQUENCE: 4
gctcatgaga aagtttactc                                                   20
```

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Probe TAQ1

<400> SEQUENCE: 5
tttgcttcag tataacgcat cgcagc                                           26

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Probe TAQ2

<400> SEQUENCE: 6
ccacatggag atacagcagt ttatgatg                                         28

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Probe TAQ3

<400> SEQUENCE: 7
ccacatggag atatagcagt ttatgatgc                                        29

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: PCR primer
      JL 223

<400> SEQUENCE: 8
cgccatacct acagctatac c                                                21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: PCR primer
      JL 224

<400> SEQUENCE: 9
gatggtttaa gcctgttcat                                                  20

<210> SEQ ID NO 10
<211> LENGTH: 302
<212> TYPE: DNA
<213> ORGANISM: Campylobacter jejuni

<400> SEQUENCE: 10
ttttgtcaaa tcagcccgta tagtgggtgc tgttataggt cgttatcacc cacatggaga      60
tacagcagtt tatgatgctt tggttagaat ggctcaagat ttttctatga gatatccaag     120
tattacagga caaggcaact tggatctat  agatggtgat agtgccgctg cgatgcgtta     180
tactgaagca aaaatgagta aactttctca tgagctttta aagatatag  ataaagatac     240

```
ggtcgatttt gttccaaatt atgatggttc agaaagcgaa cctgatgttt taccttctag      300
gg                                                                    302

<210> SEQ ID NO 11
<211> LENGTH: 302
<212> TYPE: DNA
<213> ORGANISM: Campylobacter jejuni

<400> SEQUENCE: 11
ttttgtcaaa tcagcccgta tagtgggtgc tgttataggt cgttatcacc cacatggaga       60
tatagcagtt tatgatgctt tggttagaat ggctcaagat ttttctatga gatatccaag      120
tattacagga caaggcaact ttggatctat agatggtgat agtgccgctg cgatgcgtta      180
tactgaagca aaaatgagta aactttctca tgagctttta aaagatatag ataaagatac      240
ggtcgatttt gttccaaatt atgatggttc agaaagcgaa cctgatgttt taccttctag      300
gg                                                                    302

<210> SEQ ID NO 12
<211> LENGTH: 302
<212> TYPE: DNA
<213> ORGANISM: Campylobacter jejuni

<400> SEQUENCE: 12
ttttgtcaaa tcagcccgta tagtgggtgc tgttataggt cgttatcacc cacatggaga       60
tacagcagtt tatgatgctt tggttagaat ggctcaagat ttttctatga gatatccaag      120
tattacagga caaggcaact ttggatctat agatggtgat agtgccgctg cgatgcgtta      180
tactgaagca aaaatgagta aactttctca tgagctttta aaagatatag ataaagatac      240
ggtcgatttt gttccaaatt atgatggttc agaaagcgaa cctgatgttt taccttctag      300
gg                                                                    302

<210> SEQ ID NO 13
<211> LENGTH: 302
<212> TYPE: DNA
<213> ORGANISM: Campylobacter jejuni

<400> SEQUENCE: 13
ttttgtcaaa tcagcccgta tagtgggtgc tgttataggt cgttatcatc cacatggaga       60
tacagcagtt tatgatgctt tggttagaat ggctcaagat ttttctatga gatatccaag      120
tattacagga caaggcaact ttggatctat agatggtgat agcgctgctg cgatgcgtta      180
tactgaagca aaaatgagta aactttctca tgagctttta aaagatatag ataaagatac      240
ggtcgatttt gttccaaatt atgatggttc agaaagtgaa cctgatgtct taccttctag      300
gg                                                                    302

<210> SEQ ID NO 14
<211> LENGTH: 302
<212> TYPE: DNA
<213> ORGANISM: Campylobacter jejuni

<400> SEQUENCE: 14
ttttgtcaaa tcagcccgta tagtgggtgc tgttataggt cgttatcatc cacatggaga       60
tatagcagtt tatgatgctt tggttagaat ggctcaagat ttttctatga gatatccaag      120
tattacagga caaggcaact ttggatctat agatggtgat agcgctgctg cgatgcgtta      180
tactgaagca aaaatgagta aactttctca tgagctttta aaagatatag ataaagatac      240
```

```
ggtcgatttt gttccaaatt atgatggttc agaaagtgaa cctgatgtct taccttctag    300
gg                                                                  302

<210> SEQ ID NO 15
<211> LENGTH: 302
<212> TYPE: DNA
<213> ORGANISM: Campylobacter jejuni

<400> SEQUENCE: 15
ttttgttaaa tcagcccgta tagtgggtgc tgttataggt cgttatcacc cgcatggaga     60
tacagcagtt tatgatgctt tagttagaat ggctcaagat ttttctatga gatatccaag    120
tattacagga caaggtaact ttggatctat agatggcgat agtgctgctg cgatgcgtta    180
tactgaagca aaaatgagta aactttctca tgagctttta aaagatatag ataaagatac    240
ggtcgatttt gttccaaatt atgatggttc agaaagtgaa cctgatgttt taccttctag    300
gg                                                                  302

<210> SEQ ID NO 16
<211> LENGTH: 302
<212> TYPE: DNA
<213> ORGANISM: Campylobacter coli

<400> SEQUENCE: 16
atataaaaaa tctgctcgta tagtagggga tgttatcggt aagtatcatc cacatggcga     60
tactgctgtt tacgatgcct tagtaagaat ggcacaagat ttctctatgc gttatccaag    120
tatcgatgga caaggaaact ttggttctat cgatggtgat ggcgctgctg caatgcgtta    180
tactgaagct agaatgacaa ttttagcaga agagctttta cgcgatatag ataaagatac    240
ggtagatttt gttccaaact acgatgattc tatgagtgag cccgatgttt tacctgctag    300
cg                                                                  302

<210> SEQ ID NO 17
<211> LENGTH: 302
<212> TYPE: DNA
<213> ORGANISM: Campylobacter coli

<400> SEQUENCE: 17
atataaaaaa tctgctcgta tagtagggga tgttatcggt aagtatcatc cacatggcga     60
tactgctgtt tacgatgcct tagtaagaat ggcacaagat ttctctatgc gttatccaag    120
tatcgatgga caaggaaact ttggttctat cgatggtgat ggcgctgctg caatgcgtta    180
tactgaagct agaatgacaa ttttagcaga agagctttta cgcgatatag ataaagatac    240
ggtagatttt gttccaaact acgatgattc tatgagtgag cccgatgttt tacctgctag    300
gg                                                                  302

<210> SEQ ID NO 18
<211> LENGTH: 302
<212> TYPE: DNA
<213> ORGANISM: Campylobacter lari

<400> SEQUENCE: 18
atataaaaaa tcagctcgta tagtagggga tgttataggt aagtatcatc cgcatggtga     60
tgttgctgta tatgatgctt tggttagaat ggcacaagat ttttctatgc gttatccaag    120
tgttgatgga caaggtaact ttggctctat tgatggggat ggcgctgctg ctatgcgtta    180
tactgaggct agaatgacta ttttagctga agaattgttg cgtgatattg ataaagatac    240
```

-continued

```
ggttgatttt gtaccaaatt atgatgattc tatgagtgag cctgatgttt tacctgctag     300
gg                                                                    302

<210> SEQ ID NO 19
<211> LENGTH: 302
<212> TYPE: DNA
<213> ORGANISM: Campylobacter fetus

<400> SEQUENCE: 19
atataaaaag tctgctcgta tagtaggtga tgttatcggt aagtatcacc cgcacggcga      60
tactgcggta tatgacgctt tagttagaat ggctcagaac ttttctatga gagttcctgc     120
agtagatggt caaggaaact ttggctcagt cgatggcgat ggcgcagccg ctatgcgtta     180
tactgaagct agaatgacgg ttttggcaga ggaactttta agagatttag ataaagatac     240
ggttgatttt ataccaaatt atgatgatag tttaagcgaa ccagatgttt tacccgcgcg     300
gg                                                                    302
```

METHODS FOR DETECTING AND ENUMERATING *CAMPYLOBACTER JEJUNI* IN ENVIRONMENTAL SAMPLES AND FOR IDENTIFYING ANTIBIOTIC-RESISTANT STRAINS

CROSS-REFERENCE TO RELATED APPLICATION

The application claims the benefit of U.S. Provisional Patent Application Serial Nos. 60/153,415 and 60/153,417, which were filed on Sep. 10, 1999.

STATEMENT REGARDING FEDERALLY SPONSORED RESEARCH OR DEVELOPMENT

Not applicable.

BACKGROUND OF THE INVENTION (1) Field of the Invention

The present invention relates to a process for detecting and enumerating *Campylobacter jejuni* in an environmental sample. The present invention further relates to a process which can distinguish antibiotic resistant strains of *Campylobacter jejuni* from wild-type strains, in particular, antibiotic-resistant strains resistant to high levels of ciprofloxacin. Both processes relate to PCR primers which flank a target sequence unique to *Campylobacter jejuni* in combination with one or more dual-labeled oligonucleotide probes complementary to the target sequence wherein the dual-labeled probes enable detection of PCR amplification by fluorescence detection means.

(2) Description of Related Art

Campylobacter spp. is the leading cause of gasterial enteritis in the United States, affecting millions of people annually. Of the people affected, *Campylobacter jejuni* represents the etiological agent for a large proportion of the clinical cases of Campylobacter infections in human patients. Campylobacter is a gram negative microaerophilic pathogen of both humans and animals. In humans, Campylobacter infection is characterized by acute diarrheal disease, and more recently, has been associated with Guillain Barre Syndrome, a peripheral neuropathy characterized by limb weakness, and other neurological and systemic sequelae (Hughs et al., J. Infect. Dis. 176(Suppl. 2): S92-S98 (1997); Blaser, J. Infect. Dis. 176(Suppl.): S103-S105 (1997)).

Erythromycin, fluoroquinolones, and tetracyclines are classes of antibiotics that are most frequently used to treat Campylobacter infections (Blaser, J. Infect. Dis. 176(suppl. 2): S103-S105 (1997); Altkreuse et al., Emerg. Infect. Dis. 5: 28-35 (1999)). While these antibiotic treatments are effective at controlling bacterial enteritis, increasingly, antibiotic resistant strains of *Campylobacter jejuni* are being uncovered (Gaudreau et al., Antimicrob. Agents Chemother. 42: 2106–2108 (1998); Gaunt et al., J. Antimicrob. Chemother. 37: 747–757 (1996); Moore et al., Vet. Rec. 138: 306–307 (1996); Lee et al., Internatl. J. Food Microbiol. 24: 161–170 (1994); Taylor et al., Antimicrob. Agents Chemother. 32: 1107–1112 (1988); Tenover et al., Antimicrob. Agents Chemother. 27: 37–41 (1985)). The appearance of antibiotic resistant strains of *Campylobacter jejuni* is a public health concern. Therefore, much attention has been drawn to *Campylobacter jejuni* strains which are resistant to fluoroquinolones, a class of antibiotics most frequently used for treating bacterial enteritis of which ciprofloxacin is an example.

The predominant mechanism for high-level ciprofloxacin resistance (MIC equal to or greater than 16 $\mu$g/ml) in *Campylobacter jejuni* appears to be a C to T nucleotide transition in amino acid codon 86 in the quinolone resistance determining region (QRDR) of the gyrA gene. The gyrA gene encodes one subunit of DNA gyrase, which is the target for fluoroquinolone antibiotics. The amino acid codon 86 mutation results in a threonine to isoleucine amino acid substitution in the functional gyrA protein (Wang et al., Antimicrob. Agents Chemother. 37: 457–463 (1993); Charvalos et al., J. Clin. Lab. Anal. 10: 129–133 (1996); Husmann et al., J. Clin. Microbiol. 35: 2398–2400 (1997); Gibreel et al., Antimicrob. Agents Chemother. 42: 3276–3278 (1998); Ruiz et al., Microbiol. Immunol. 42: 223–226 (1998)). Ciprofloxacin susceptibility testing of Campylobacter is commonly performed using standard methods such as broth or agar dilution (Charvalos et al., ibid.; Gaunt et al., ibid.; Gaudreau et al., ibid.; Ruiz et al., ibid.) which are tedious and time consuming methods.

In order to conduct adequate epidemiological studies to determine the sources of *Campylobacter jejuni* in the agricultural environment, a sensitive diagnostic test is desirable. The appropriate test would allow execution of surveillance programs to monitor contamination of food and the environment in a timely manner. Therefore, the test most appropriate is a test of high sensitivity, specificity, and short turn-around time.

Currently, the standard method for isolation and identification of *Campylobacter jejuni* involves a pre-enrichment step in supplemental broth and incubation for between about 24 and 48 hours under suitable growth conditions. Next, there follows an isolation step by subculturing the enrichment broth onto Campylobacter selective media and incubation for an additional 24 to 72 hours. The identity of isolated colonies of Campylobacter from selective media can be confirmed using biochemical tests or polymerase chain reaction (PCR) methods. Antibiotic susceptible or resistant Campylobacter strains can be identified using particular susceptibility/resistance testing which requires an additional 24 hours for completion. Thus, to identify antibiotic-resistant strains of *Campylobacter jejuni* in an environmental sample requires an average of four and a half days to complete.

Therefore, there is a need for a test of improved sensitivity, and specificity, and further of short turn-around time that would enable detection and enumeration of *Campylobacter jejuni* in environmental samples. With the appearance of strains which are antibiotic resistant, there is a further need for a rapid and sensitive test that will detect these antibiotic-resistant strains in an environmental sample.

SUMMARY OF THE INVENTION

The present invention provides a process for detecting and enumerating *Campylobacter jejuni* in an environmental sample. The present invention further provides a process which can distinguish antibiotic resistant strains of *Campylobacter jejuni* from wild-type strains, in particular, antibiotic-resistant strains resistant to high levels of ciprofloxacin. Both processes use PCR primers which flank a target sequence unique to *Campylobacter jejuni* in combination with one or more dual-labeled oligonucleotide probes complementary to the target sequence wherein the dual-labeled probes enable detection of PCR amplification by fluorescence detection means.

Therefore, the present invention provides a process for detecting and enumerating *Campylobacter jejuni* in a sample, the process comprising: (a) providing in a PCR reaction mixture a sample suspected to contain a target nucleic acid sequence that is unique to *Campylobacter jejuni*, a first oligonucleotide PCR primer and a second oligonucleotide PCR primer which hybridize to opposite strands of the target nucleic acid sequence and flank the target nucleic acid sequence for PCR amplification of the target nucleic acid sequence, each of four deoxynucleoside triphosphates selected from the group consisting of adenosine, guanosine, thymidine, cytosine, and analogs thereof, a nucleic acid polymerase having a 5' to 3' exonuclease activity and lacking 3' to 5' exonuclease activity, and an oligonucleotide probe blocked against chain extension at its 3' end and labeled at its 5' with an energy transfer donor fluorophore and labeled at its 3' end with an energy transfer acceptor fluorophore wherein the oligonucleotide probe is complementary to the target nucleic acid; (b) amplifying the target nucleic sequence in the sample under suitable PCR reaction mixture temperature conditions by a repetitive series of PCR thermal cycling steps comprising: (1) denaturing the target nucleic acid sequence into opposite strands; (2) hybridizing the first and second oligonucleotide PCR primers and the oligonucleotide probe to the denatured strands, and (3) extending the hybridized primers with the four deoxynucleoside triphosphates and the nucleic acid polymerase, and producing 5' fluorophore and 3' fluorophore labeled nucleotide fragments during the extension phase by the 5' to 3' exonuclease activity of the nucleic acid polymerase on the oligonucleotide probe annealed to the denatured strands; (c) following amplification of the target nucleic acid sequence by one or more series of the thermal cycling steps, spectrophotometrically detecting and measuring the amount of fluorescence of the 5' fluorophore labeled nucleotide fragments wherein the fluorescence indicates the sample contains the *Campylobacter jejuni* and wherein the amount of fluorescence is proportional to the number of *Campylobacter jejuni* in the sample.

In a preferred embodiment of the present invention, the target nucleic acid sequence is a nucleotide sequence from QRDR of gyrA, 16S rDNA, or flaA/flaB of *Campylobacter jejuni*. In particular, wherein the target nucleic acid sequence is the nucleotide sequence in SEQ ID NO:10 and wherein the first and second oligonucleotide PCR primers and the oligonucleotide probe are complementary to the target nucleic acid sequence. In a most preferred embodiment, the first oligonucleotide primer has the nucleotide sequence set forth in SEQ ID NO:3 and the second oligonucleotide PCR primer has the nucleotide sequence set forth in SEQ ID NO:4 and the oligonucleotide probe has the nucleotide sequence set forth in SEQ ID NO:5.

The present invention further provides for a process for detecting and enumerating *Campylobacter jejuni* wherein the sample comprises a culture from which an environmental sample containing the *Campylobacter jejuni* is cultivated; or wherein the sample comprises the *Campylobacter jejuni* which is isolated from an environmental sample by immunomagnetic separation; or wherein the sample comprises amplified DNA produced by a PCR using a first primer selected from SEQ ID NO:3 and SEQ ID NO:8 and a second primer selected from the group consisting of SEQ ID NO:4 and SEQ ID NO:9.

The present invention further provides a process for detecting in a sample antibiotic-resistant *Campylobacter jejuni* and wild-type *Campylobacter jejuni*, in particular wherein the antibiotic-resistant *Campylobacter jejuni* is resistant to ciprofloxacin, the process comprising: (a) providing in a PCR reaction mixture a sample suspected to contain a target nucleic acid sequence that is unique to *Campylobacter jejuni*, a first oligonucleotide PCR primer and a second oligonucleotide PCR primer which hybridize to opposite strands of the target nucleic acid sequence and flank the target nucleic acid sequence for PCR amplification of the target nucleic acid sequence, each of four deoxynucleoside triphosphates selected from the group consisting of adenosine, guanosine, thymidine, cytosine, and analogs thereof, a nucleic acid polymerase having a 5' to 3' exonuclease activity and lacking 3' to 5' exonuclease activity, a first oligonucleotide probe blocked against chain extension at its 3' end and labeled at its 5' with a first energy transfer donor fluorophore and labeled at its 3' end with an energy transfer acceptor fluorophore, and a second oligonucleotide probe blocked against chain extension at its 3' end and labeled at its 5' with a second energy transfer donor fluorophore and labeled at its 31 end with an energy transfer acceptor fluorophore, wherein the first donor fluorophore emits fluorescent light of a different wavelength than the second donor fluorophore, and wherein the first oligonucleotide probe is complementary to the target nucleic acid from the wild-type *Campylobacter jejuni* and the second oligonucleotide probe is complementary to the target from the antibiotic-resistant *Campylobacter jejuni*; (b) amplifying the target nucleic sequence in the sample under suitable PCR reaction mixture temperature conditions by a repetitive series of PCR thermal cycling steps comprising: (1) denaturing the target nucleic acid sequence into opposite strands; (2) hybridizing the first and second oligonucleotide PCR primers and the first and second oligonucleotide probes to the denatured strands, and (3) extending the hybridized primers with the four deoxynucleoside triphosphates and the nucleic acid polymerase, and producing 5' fluorophore and 3' fluorophore labeled nucleotide fragments during the extension phase by the 5' to 3' exonuclease activity of the nucleic acid polymerase on the oligonucleotide probe annealed to the denatured strands; (c) following amplification of the target nucleic acid sequence by one or more series of the thermal cycling steps, spectrophotometrically detecting and measuring an amount of fluorescence of the 5' fluorophore labeled nucleotide fragments wherein fluorescence of the first fluorophore indicates the sample contains wild-type Campylobacter jejuni and fluorescence of the second fluorophore indicates the sample contains antibiotic-resistant *Campylobacter jejuni* and wherein a ratio of the first and second fluorescence is proportional to the ratio of the wild-type and the antibiotic-resistant *Campylobacter jejuni* in the sample.

In a preferred embodiment of the process of the present invention relating to allelic discrimination, the target nucleic acid sequence is a nucleotide sequence from QRDR of gyrA, 16S rDNA, or flaA/flaB of *Campylobacter jejuni*. In particular, wherein the target nucleic acid sequence is the nucleotide sequence in SEQ ID NO:10 and wherein the first and second oligonucleotide PCR primers and the oligonucleotide probe are complementary to the target nucleic acid sequence. In a most preferred embodiment, the first oligonucleotide primer has the nucleotide sequence set forth in SEQ ID NO:3 and the second oligonucleotide PCR primer has the nucleotide sequence set forth in SEQ ID NO:4 and wherein the first oligonucleotide probe has the nucleotide sequence set forth in SEQ ID NO:6 and the second oligonucleotide probe has the nucleotide sequence set forth in SEQ ID NO:7.

The present invention further provides for a process for distinguishing antibiotic-resistant *Campylobacter jejuni* from antibiotic-susceptible *Campylobacter jejuni* wherein the sample comprises a culture from which an environmental sample containing the *Campylobacter jejuni* is cultivated;

or wherein the sample comprises the *Campylobacter jejuni* which is isolated from an environmental sample by immunomagnetic separation; or wherein the sample comprises amplified DNA produced by a PCR using a first primer selected from SEQ ID NO:3 and SEQ ID NO:8 and a second primer selected from the group consisting of SEQ ID NO:4 and SEQ ID NO:9.

The present invention further provides a kit for detecting *Campylobacter jejuni* in a sample comprising in one or more containers: (a) a first oligonucleotide primer; and (b) a second oligonucleotide primer, wherein the first and second oligonucleotides primers hybridize to opposite strands of a target sequence unique to *Campylobacter jejuni* and flank the target nucleic acid sequence for PCR amplification of the target nucleic acid sequence. In a preferred embodiment of the present invention, the kit further comprises an oligonucleotide probe blocked against chain extension at its 3' end and labeled at its 5' with an energy transfer donor fluorophore and labeled at its 3' end with an energy transfer acceptor fluorophore wherein the oligonucleotide probe is complementary to the target nucleic acid sequence and wherein the oligonucleotide probe enables fluorescence detection and enumeration of the *Campylobacter jejuni*. In a most preferred embodiment, the target nucleic acid sequence is a nucleotide sequence from QRDR of gyrA, 16S rDNA, or flaA/flaB of *Campylobacter jejuni*. In particular, a kit wherein the first primer has the nucleotide sequence set forth in SEQ ID NO:3, the second oligonucleotide PCR primer has the nucleotide sequence set forth in SEQ ID NO:4, and the oligonucleotide probe has the nucleotide sequence set forth in SEQ ID NO:5.

In an embodiment further still, the kit comprises in one or more containers at least one of an optimized buffer for the reaction, a control nucleic acid comprising the target nucleic acid sequence, nucleoside triphosphates selected from the group consisting of adenosine, guanosine, thymidine, cytosine, and analogs thereof, a polymerase, a primer with the sequence set forth in SEQ ID NO:8, or a primer with the sequence set forth in SEQ ID NO:9.

The present invention further provides a kit for detecting antibiotic-resistant and wild-type *Campylobacter jejuni* in a sample, in particular wherein the antibiotic-resistant *Campylobacter jejuni* is resistant to ciprofloxacin, comprising in one or more containers: (a) a first oligonucleotide primer; (b) a second oligonucleotide primer; (c) a first oligonucleotide probe; and (d) a second oligonucleotide probe, wherein the first and second oligonucleotide primers hybridize to opposite strands of a target sequence unique to *Campylobacter jejuni* and flank the target nucleic acid sequence for PCR amplification of the target nucleic acid sequence, wherein the first and second oligonucleotide probes are blocked against chain extension at its 3' end and labeled at the 5' with a an energy transfer donor fluorophore and labeled at the 3' end with an energy transfer acceptor fluorophore, wherein the donor fluorophore on the first oligonucleotide probe emits fluorescent light of a different wavelength than the donor fluorophore on the second oligonucleotide probe, and wherein the first oligonucleotide probe is complementary to the target nucleic acid from the wild-type *Campylobacter jejuni* and the second oligonucleotide probe is complementary to the target from the antibiotic-resistant *Campylobacter jejuni*.

In a preferred embodiment, the target nucleic acid sequence is a nucleotide sequence from QRDR of gyrA, 16S rDNA, or flaA/flaB of *Campylobacter jejuni*. Preferably, wherein the first primer has the nucleotide sequence set forth in SEQ ID NO:3, the second oligonucleotide PCR primer has the nucleotide sequence set forth in SEQ ID NO:4, the first oligonucleotide probe has the nucleotide sequence set forth in SEQ ID NO:6, and the second oligonucleotide probe has the nucleotide sequence set forth in SEQ ID NO:7.

In an embodiment further still, the kit comprises in one or more containers at least one of an optimized buffer for the reaction, a control nucleic acid comprising the target nucleic acid sequence, nucleotide triphosphates selected from the group consisting of adenosine, guanosine, thymidine, cytosine, and analogs thereof, a polymerase, a primer with the sequence set forth in SEQ ID NO:8, or a primer with the sequence set forth in SEQ ID NO:9.

The present invention further provides a labeled nucleic acid probe for detecting *Campylobacter jejuni* DNA comprising the nucleotide sequence 5'-TTTGCTTCAGTATAACGCATCGCAGC-3' (SEQ ID NO:5) and a labeled nucleic acid probe for detecting Campylobacter jejuni DNA resistant to an antibiotic comprising the nucleotide sequence 5'-CCACATGGAGATATAGCAGTTTATGATGC-3' (SEQ ID NO:7). In a preferred embodiment, the probe is labeled at its 5' end with an energy transfer donor fluorophore and labeled at its 3' end with an energy transfer acceptor fluorophore. Preferably, the probe is blocked against chain extension at its 3' end.

In any one of the above embodiments of the present invention, the fluorophore is preferably selected from the group consisting of fluorescein, 5-carboxyfluorescein (FAM), 2',7'-dimethoxy-4',5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), tetrachloro-6-carboxy-fluorescein (TET), VIC, and 5-(2'-aminoethyl)aminonaphthalene-1-sulfonic acid (EDANS).

Finally, the present invention provides a process for detecting *Campylobacter jejuni* in a sample, the process comprising: (a) providing in a PCR reaction mixture a sample suspected to contain a target nucleic acid sequence that is unique to *Campylobacter jejuni*, a first oligonucleotide PCR primer and a second oligonucleotide PCR primer which hybridize to opposite strands of the target nucleic acid sequence and flank the target nucleic acid sequence for PCR amplification of the target nucleic acid sequence, each of four deoxynucleoside triphosphates selected from the group consisting of adenosine, guanosine, thymidine, cytosine, and analogs thereof, and a nucleic acid polymerase having a 5' to 3' exonuclease activity and lacking 3' to 5' exonuclease activity; (b) amplifying the target nucleic sequence in the sample under suitable PCR reaction mixture temperature conditions to provide a detectable amount of amplified target nucleic acid sequence by a repetitive series of PCR thermal cycling steps comprising: (1) denaturing the target nucleic acid sequence into opposite strands; (2) hybridizing the first and second oligonucleotide PCR primers and the oligonucleotide probe to the denatured strands, and (3) extending the hybridized primers with the four deoxynucleoside triphosphates and the nucleic acid polymerase; and (c) detecting the amplified target nucleic acid sequence.

Preferably, the target nucleic acid sequence is a nucleotide sequence from QRDR of gyrA, 16S rDNA, or flaA/flaB of *Campylobacter jejuni*. In particular, wherein the target nucleic acid sequence is the nucleotide sequence in SEQ ID NO:10 and wherein the first and second oligonucleotide PCR primers are complementary to the target nucleic acid sequence. Most particularly, the first oligonucleotide primer has the nucleotide sequence set forth in SEQ ID NO:3 and the second oligonucleotide PCR primer has the nucleotide sequence set forth in SEQ ID NO:4.

In a further embodiment of the above process, a labeled probe selected from the group consisting of SEQ ID NO:6 and SEQ ID NO:7 is hybridized to the amplified target nucleic acid sequence to determine whether the *Campylobacter jejuni* is antibiotic-resistant.

OBJECTS

Therefore, it is an object of the present invention to provide a process for detecting and enumerating *Campylobacter jejuni* in an environmental sample.

It is also an object of the present invention to provide a process for detecting in an environmental sample antibiotic-resistant *Campylobacter jejuni* from antibiotic susceptible *Campylobacter jejuni*.

It is further an object of the present invention to be able to detect and quantify *Campylobacter jejuni* in a sample without the need to purify genomic DNA, and further to directly detect *Campylobacter jejuni* in an environmental sample, which includes but is not limited to, fecal matter, food, soil, and water, without the need to culture the microorganism.

DESCRIPTION OF THE DRAWINGS

FIG. 3 shows multiple nucleotide sequence alignments of selected Campylobacter isolates. The alignment represents a 300 bp nucleic acid fragment of gyrA that includes the QRDR nucleic acid sequence. The *Campylobacter jejuni* QRDR sequence hybridizing to PCR oligonucleotide primers, JL 238 and JL 239, and to oligonucleotide probes TAQ1, TAQ2, and TAQ3 are shown. Amino acid codon 86, which is positioned at nucleotides 62–64, is shown underlined. cj33560cr6 and cj33292cr216 are ciprofloxacin-resistant isolates and contain the C to T transition in amino acid codon 86. The DNA sequences for *Campylobacter jejuni* strains cj33291 (SEQ ID NO:10), cj33560 (SEQ ID NO:11), cj33560cr6 (SEQ ID NO:12), cj33292 (SEQ ID NO:13), cj33292cr216 (SEQ ID NO:14), and cj49349 (SEQ ID NO:15) are shown and compared to the DNA sequences for *Campylobacter coli* strain cc1777708 (SEQ ID NO:16), *Campylobacter coli* strain cc43473 (SEQ ID NO:17), *Campylobacter lari* strain c143675 (SEQ ID NO:18), and *Campylobacter fetus* strain cf27374 (SEQ ID NO:19).

FIG. 6 shows the results of a detection assay performed according to the present invention. The fluorescent signal of the reporter dye is recorded on the y-axis. The PCR cycle is indicated on the x-axis. The reporter emission was monitored during the reaction and is directly proportional to the amount of PCR product accumulated. The bold line represents the threshold setting and was used to determine a positive reaction. (A) shows the results using the TAQ2 probe. (B) shows the results using the TAQ1 probe. The JL 238 and JL 239 primers were used in the reactions shown in (A) and (B). Each chromosomal sample was assayed in duplicate. The *Campylobacter coli* samples in both (A) and (B) did not produce a threshold surpassing signal after 40 PCR cycles. A *Campylobacter jejuni* sample that produced a similar signal would be considered negative for *Campylobacter jejuni*. The one femtogram *Campylobacter jejuni* reactions were negative in (A); however, one of these samples tested positive in (B).

FIG. 8 shows amplification plots of wild-type and ciprofloxacin-resistant *Campylobacter jejuni* strains from an allelic discrimination assay performed according to the present invention. In the assay, both FAM (wild-type) and TET (resistant) reporter probes are included in the assay reaction. A sample with *Campylobacter jejuni* produces both FAM and TET signals above background levels. The relative fluorescent emissions after the final PCR cycle determine if a *Campylobacter jejuni* sample contains DNA from a wild-type or resistant microorganism. cj33560 and cj49349 are wild-typ strains and cj33292cr2162 is resistant to ciprofloxacin because of the C to T transition in amino acid codon 86. Each reaction contained 10 ηg of chromosomal DNA.

Figure 12:
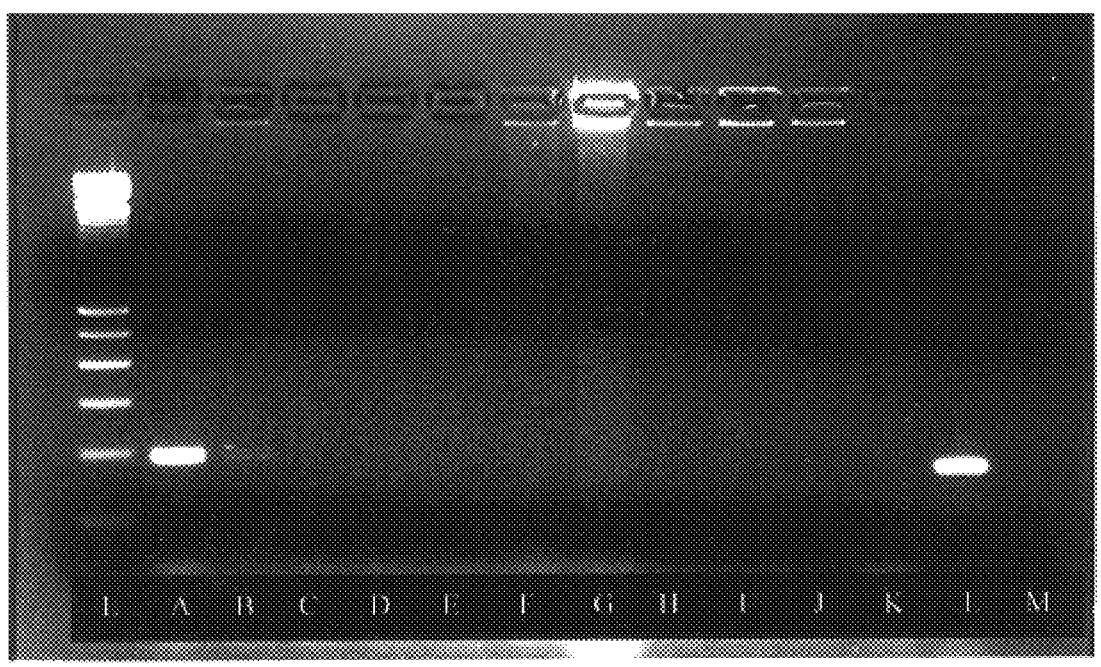

FIG. 12 shows an agarose gel stained with ethidium bromide of PCR products from cells isolated by immunomagnetic separation of fecal samples spiked with Campylobacter jejuni cj43429 (lane A), Campylobacter coli cc1777208 (lane E), or both (lanes B, C, D, G, H, I).

Figure 13:
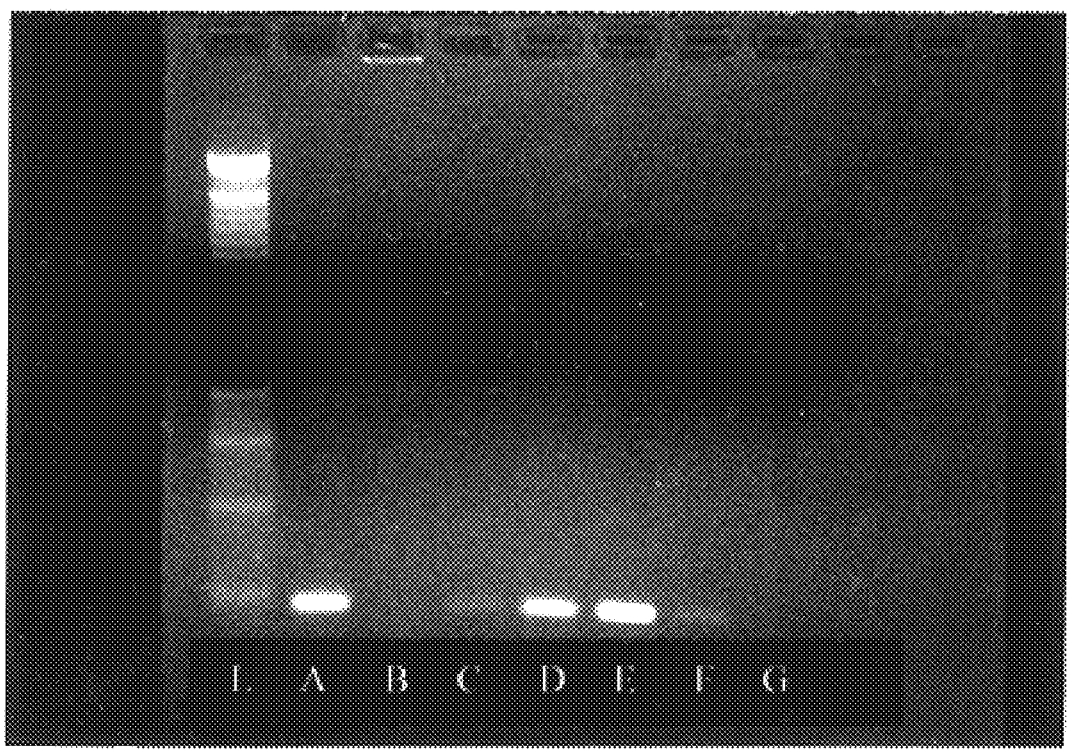

FIG. 13 shows an agarose gel stained with ethidium bromide of the PCR products from concentrations of Campylobacter jejuni cj43429 ranging from $10^9$ CFU/ml to $10^4$ CFU/ml (lanes B–F).

Figure 14:
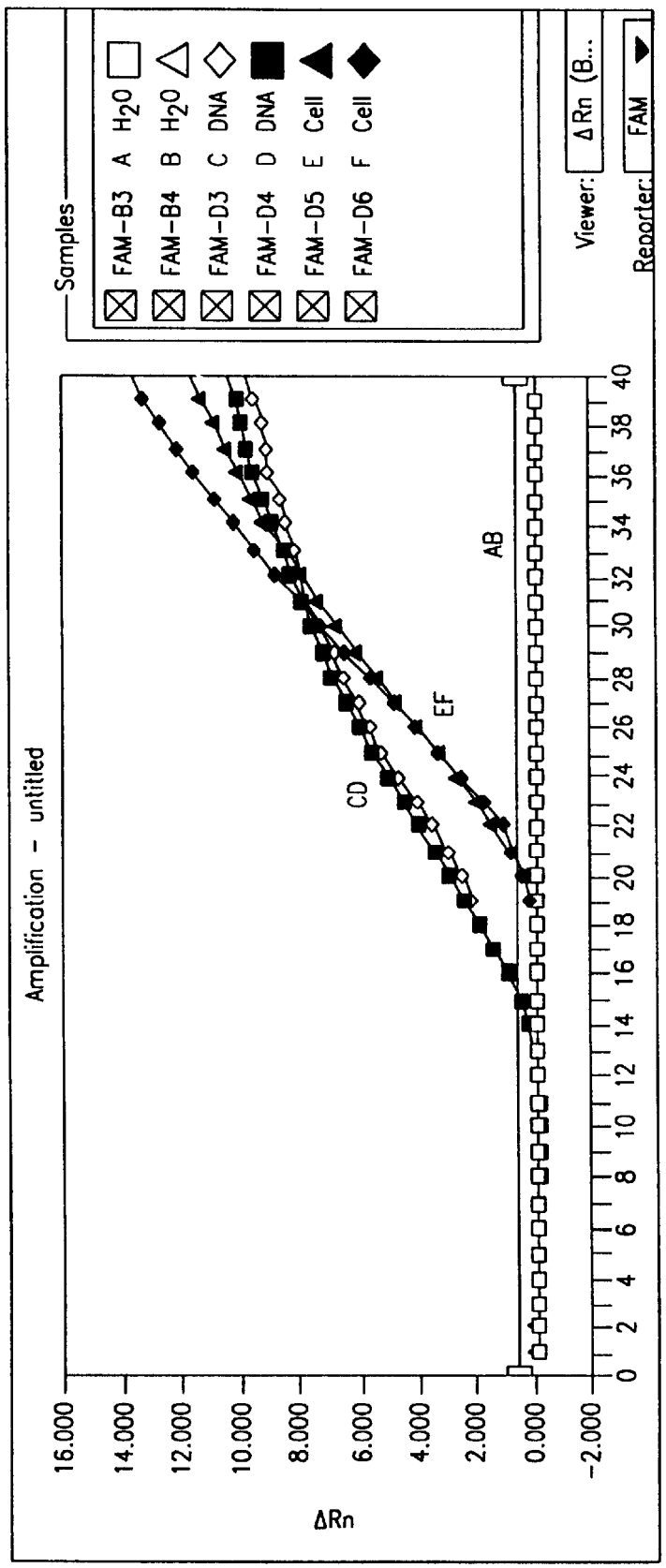

FIG. 14 shows the ability of the TAQMAN PCR to detect 200 Campylobacter jejuni cj43429 cells after 21 PCR cycles (E–F) compared to 10 ηg of cj43429 DNA (C–D).

DETAILED DESCRIPTION OF THE INVENTION

The present invention provides a method for the rapid and sensitive identification of Campylobacter jejuni in an environmental sample, and further, the present invention provides a rapid and sensitive method for distinguishing antibiotic resistant mutant strains of Campylobacter jejuni from antibiotic susceptible strains. Further still, the present invention provides a method for enumerating the number of Campylobacter jejuni, mutant and/or wild-type, in an environmental sample.

In particular, the present invention uses polymerase chain reaction (PCR) wherein an oligonucleotide probe is complementary to a target nucleic acid sequence of Campylobacter jejuni and an oligonucleotide PCR primer pair wherein a first primer comprises a nucleotide sequence complementary to sequence flanking the 5' end of the target nucleic acid sequence and a second primer comprises a nucleotide sequence complementary to a nucleotide sequence flanking the 3' end of the target nucleic acid sequence. The nucleotide sequences comprising the oligonucleotide probe and oligonucleotide PCR primers are specific to Campylobacter jejuni and do not cross-react with other related or unrelated microorganisms.

The oligonucleotide probe is a dual-labeled oligonucleotide probe which is labeled at the 5' end and the 3' end with donor and/or acceptor moieties of molecular energy transfer pairs. In particular, the moieties on the dual-labeled probe can be fluorophores, such that the fluorescent energy of the donor is absorbed or quenched by an acceptor in proximity to the donor. U.S. Pat. No. 5,866,336 to Nazarenko et al. discloses particular molecular energy transfer labels and methods for their use in oligonucleotide primers in nucleic amplification methods. U.S. Pat. No. 5,866,336 is hereby incorporated herein by reference. Common fluorophores suitable for use as donor-acceptor pairs in the present invention, include but are not limited to, fluorescein, 5-carboxyfluorescein (FAM), 2',7'-dimethoxy-4',5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), tetrachloro-6-carboxy-fluorescein (TET), VIC (Perkin-Elmer Biosystems), and 5-(2'-aminoethyl) aminonaphthalene-1-sulfonic acid (EDANS). Whether a fluorophore is an acceptor (quencher) or a donor is defined by its excitation and emission spectra. For example, FAM is a suitable donor fluorophore for use with JOE, TAMRA, and ROX which quenches the fluorescence of the donor. In a preferred embodiment, the dual-labeled oligonucleotide probe is labeled at the 5' end with the donor fluorophore FAM, VIC, or TET and at the 3' end with acceptor or quencher fluorophore TAMRA.

Figure 1:
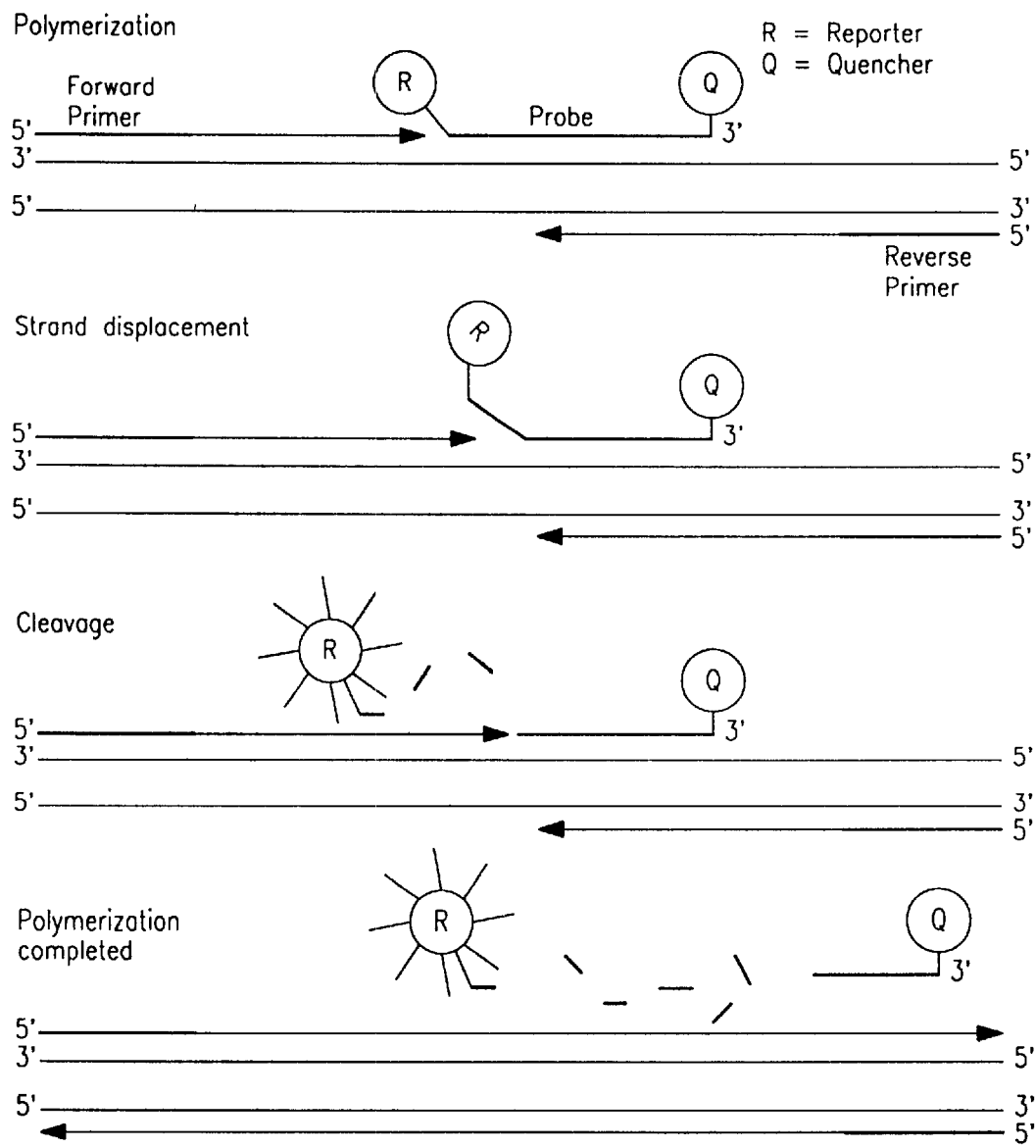
FIG. 1 is a schematic diagram of PCR amplification and detection with fluorogenic probes.
Figure 2:
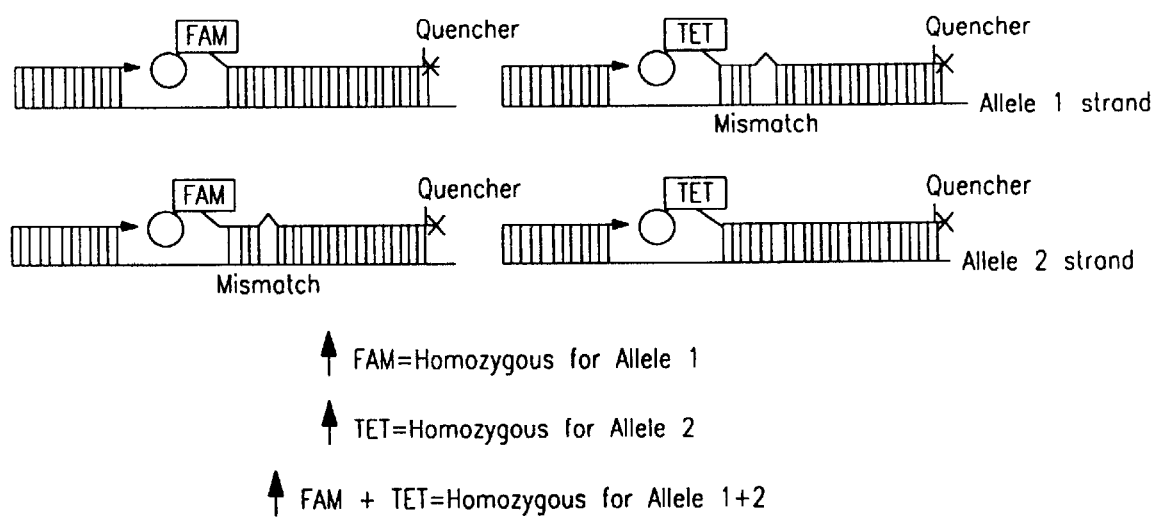
FIG. 2 is a schematic diagram of the allelic discrimination assay design strategy with fluorogenic probes.
Figure 4:
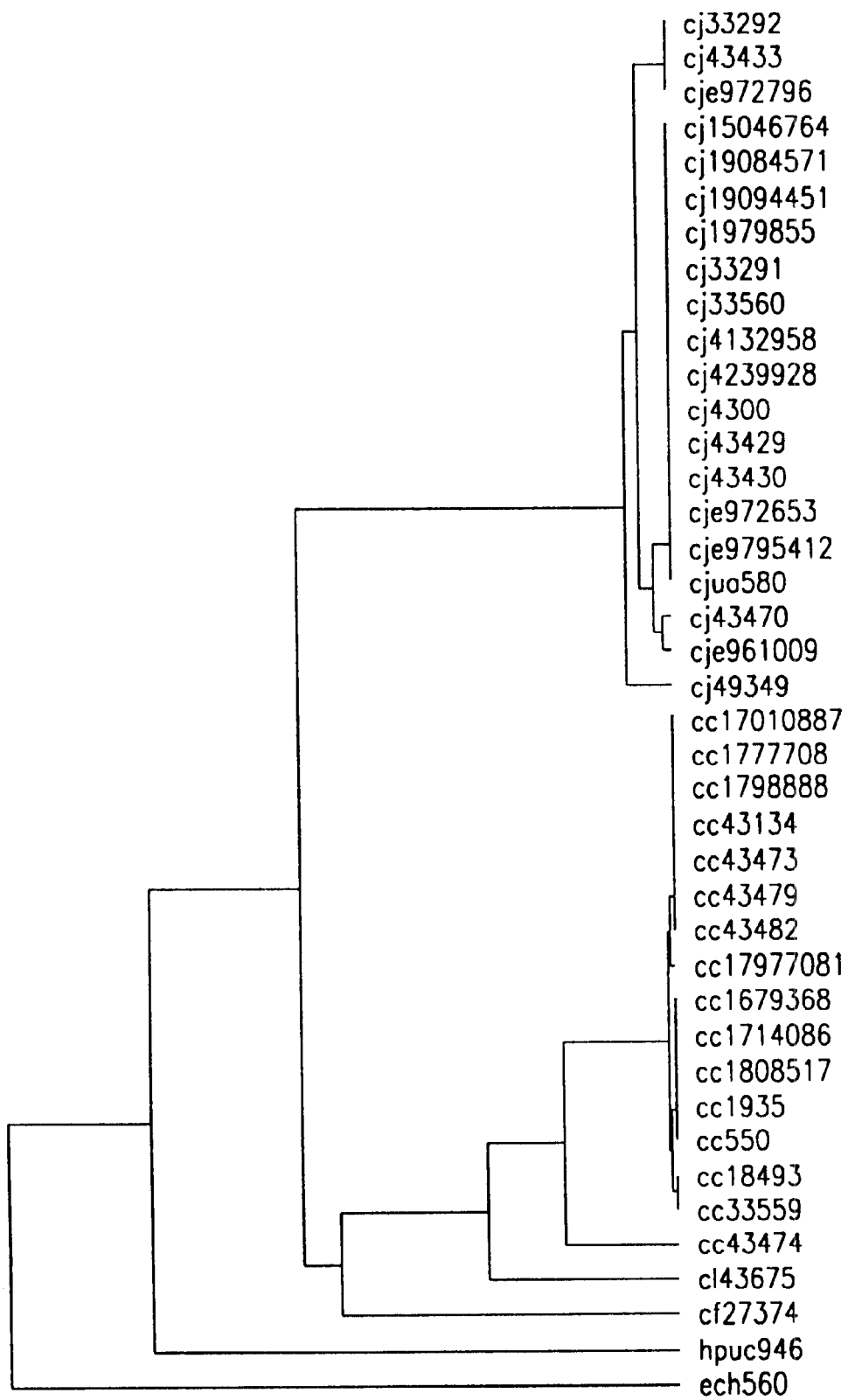
FIG. 4 shows a phylogram analysis of Campylobacter strains. The phylogram is based on the 300 bp nucleic acid fragment of the Campylobacter QRDR sequence in the gyrA shown in FIG. 1. The lengths of the horizontal lines represent the degree of relatedness between the nucleotide sequences of the individual strains.

The use of dual-labeled oligonucleotide probes in PCR reactions is disclosed in U.S. Pat. No. 5,716,784 to DiCesare which is hereby incorporated herein by reference. In the PCR reaction of the present invention, the dual-labeled fluorescent oligonucleotide probe binds to the target nucleic acid between the flanking oligonucleotide PCR primers during the annealing step of the PCR reaction (see FIG. 1). The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe releases the 5' reporter fluor, from the blocking effect of the 3' quenching fluor. The fluorescence of the reporter fluor is detected and monitored during the reaction. The amount of detected fluorescence is proportional to the amount of fluorescent product released. The detection can be accomplished by any means which can detect fluorescence. A method and detection system that is particularly useful in practicing the present invention is the PCR-based TAQMAN technology (Heid et al., Genome Res. 6: 986–994 (1996)). TAQMAN is a registered trademark of Roche Molecular Systems, Inc. (Alameda, Calif.). Methods and apparatus for performing TAQMAN-based reactions and detecting the reaction products are available from Applied Biosystems Division, Perkin-Elmer, Foster City, Calif. Because TAQMAN technology employs the donor-acceptor technology described above and an apparatus to detect fluorescence by the reporter fluor during the PCR reaction, the TAQMAN technology allows for the rapid and real-time detection and enumeration of target sequences during the PCR reaction. Thus, the TAQMAN technology provides a means for characterizing PCR products without the need for gel electrophoresis following the PCR reaction. Therefore, the oligonucleotide PCR primers and the dual-labeled oligonucleotide probes used according to the method of the present invention provides a means not only for real-time detection and identification of Campylobacter in an environmental sample, but also a real-time means for enumerating or quantifying the number of Campylobacter jejuni microorganisms in the sample.

The requirement for the oligonucleotide PCR primers and oligonucleotide probes for practicing the present invention is that the oligonucleotide PCR primers and oligonucleotide probes be specific for Campylobacter jejuni nucleic acid sequences and not cross-react with nucleic acids from closely related members of the genera or unrelated members of the Enterobacteriaceae, and not amplify spurious unrelated nucleic acids. Target nucleic acid sequences, which can enable Campylobacter jejuni to be distinguished from other Campylobacters include, but are not limited to, particular nucleic acid sequences within the flaA/flaB genes that are unique to Campylobacter jejuni, particular nucleic acid sequences at the 3' end of the 16S rDNA that are unique to Campylobacter jejuni, and particular nucleic acid sequences in the gyrA gene that are unique to Campylobacter jejuni. A suitable upstream flaA oligonucleotide PCR primer includes the unique nucleic acid sequence of the coding strand located between nucleotide 1742 and 1766 and a suitable downstream flaB oligonucleotide PCR primer includes the unique nucleic acid sequence between nucleotides 1950 and 1929. These oligonucleotide PCR primers define a 178 bp region. A dual-labeled probe is provided to a unique nucleic acid sequence located between the upstream and downstream oligonucleotide PCR primers.

In a preferred embodiment of the present invention, the oligonucleotide PCR primer pair targets the QRDR region of the gyrA gene and the probe is complementary to a sequence within the target sequence. The PCR primer pair comprises oligonucleotide PCR primer JL 238, which comprises the nucleotide sequence 5'-TGGGTGCTGTTATAGGTCGT-3' (SEQ ID NO:3), and oligonucleotide PCR primer JL 239, which comprises the nucleotide sequence 5'-GCTCATGAGAAAGTTTACTC-3' (SEQ ID NO:4). The primer pair flanks the QRDR target sequence. The oligonucleotide probe TAQ1, which comprises the nucleotide sequence 5'-TTTGCTTCAGTATAACGCATCGCAGC-3' (SEQ ID NO:5), is complementary to the target sequence. TAQ1 is labeled at the 5' end with an energy transfer donor fluorophore and at the 3' end with an energy transfer acceptor fluorophore. Preferably, TAQ1 has the energy transfer donor fluorophore, FAM, at the 5' end and the energy transfer acceptor fluorophore, TAMRA, at the 3' end. The oligonucleotide PCR primers define a 192 bp nucleic acid sequence of the QRDR of gyrA. The nucleic acid sequence for primer JL 238 was selected because it showed 100% nucleic acid sequence identity to nucleic acids sequenced from 27 of 28 Campylobacter jejuni strains. Campylobacter jejuni E961009 was the single exception; its nucleic acid contained only a one base mismatch (95% identity) with primer JL 238. A substantial lack of nucleic acid sequence identity to the JL 238 primer was found in gyrA QRDR sequences of Campylobacter coli (65% identity, Campylobacter lari (70% identity), Campylobacter fetus (70% identity), Campylobacter upsaliensis (65% identity), Campylobacter hyoilei (65% identity), Helicobacter pylori (70% identity), Escherichia coli (60% identity), Enterobacter cloacae (60% identity), Klebsiella pneumoniae (60% identity), and Erwina carotovora (60% identity). Significantly, the last three 3' nucleotides in JL 238 are mismatched with all the gyrA QRDR nucleic acids of the species analyzed except for Campylobacter jejuni.

Figure 5:
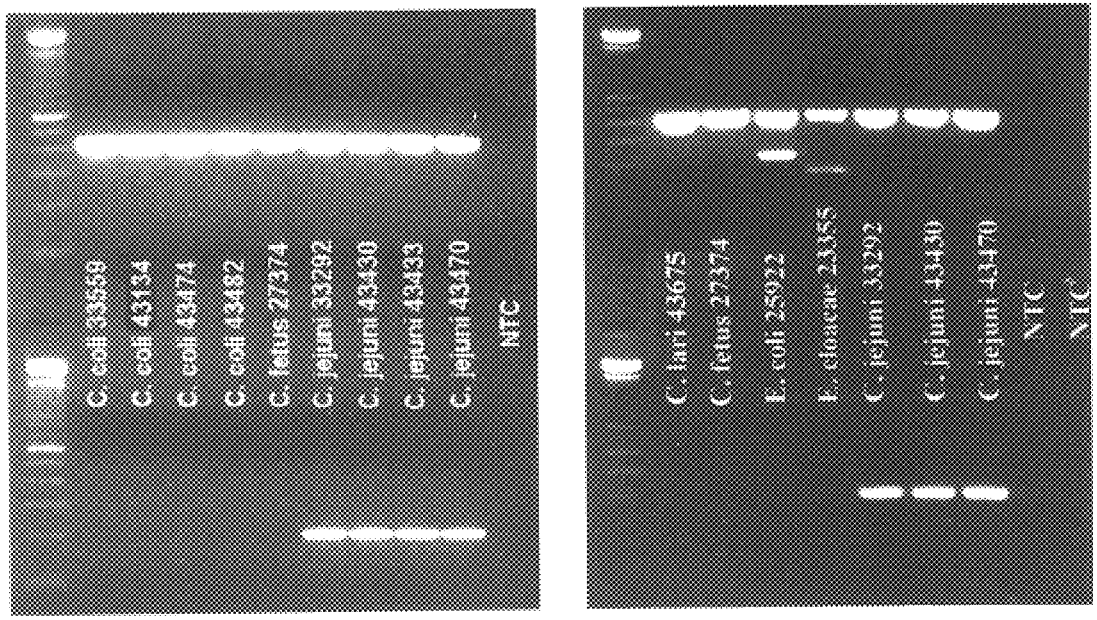
FIG. 5 shows agarose gel electrophoresis of PCR reactions stained with ethidium bromide. The first tier of each gel shows the DNA amplicons produced from the QRDR nucleic acid sequencing primers. The smaller DNA amplicons in the *E. coli* and *Erwina cloacae* lanes are non-specific PCR products. The second tier of each gel shows the amplification products produced with primers JL 238 and JL 239. 100 bp markers are in the first lanes and no DNA controls are in the far right-hand lanes. Each lane was loaded with 20 µl of a 50 µl PCR reaction mixture. The PCR conditions were as specified herein except that Platinum Taq DNA polymerase (Life technologies, GIBCO BRL, Grand Island, N.Y.) was the polymerase used for the PCR reactions. Also, the concentration of each DNTP was 0.2 mM, and the $MgCl_2$ concentration was 1.5 mM. Oligonucleotide probes and buffer, AMPERASE, Tween 20, and gelatin were not included in these reactions. The term "NTC" refers to no template (DNA) control.

Similarly, the JL 239 primer was designed for its 100% nucleic acid sequence identity with all Campylobacter jejuni nucleic acid sequences analyzed, and its lack of nucleic acid sequence identity with the gyrA QRDR nucleic acid sequences from Campylobacter coli (50% identity, Campylobacter lari (50% identity), Campylobacter fetus (40% identity), Campylobacter upsaliensis (55% identity), Campylobacter hyoilei (50% identity), Helicobacter pylori (45% identity), Escherichia coli (65% identity), Enterobacter cloacae (65% identity), Klebsiella pneumoniae (55% identity), and Erwina carotovora (70% identity). The specificity of these oligonucleotide PCR primers is sufficient to distinguish between isolates of Campylobacter jejuni and other bacterial species examined by standard PCR methods as shown in FIG. 5. The positioning of the JL 238 and JL 239 primers to target the target sequence that includes amino acid codon 86 (shown in FIG. 3) was also important for the development of the allelic discrimination assay of the present invention.

Probe TAQ1 was designed for the purpose of Campylobacter jejuni identification and was, therefore, localized to a nucleic acid sequence between the sequences complementary to JL 238 and JL 239 which was 100% conserved among all Campylobacter jejuni isolates. It was not necessary for this oligonucleotide probe to distinguish between nucleic acids from different species of Campylobacter because primers JL 238 and JL 239 served this purpose. However, it was necessary for the oligonucleotide probe to anneal to all Campylobacter gyrA QRDR nucleic acids. Probe TAQ1 did show nucleic acid sequence identity with Campylobacter coli nucleic acids ranging from 88 to 92%. The donor fluorophore, preferably FAM or TET, was attached to the 5' nucleotide of the oligonucleotide probe and an acceptor fluorophore, preferably TAMRA, was positioned at the 3' nucleotide of the oligonucleotide probe. The oligonucleotide probe was phosphorylated at the 3' end in order to block chain extension of the oligonucleotide probe during PCR amplification.

Primer JL 238 has a Tm of 60° C., primer JL 239 has a Tm of 56° C., and probe TAQ1 has a Tm of 62.3° C. The term "Tm" as used herein means the temperature wherein 50% of a given oligonucleotide is hybridized to its complementary strand. For oligonucleotides less than 21 nucleotides, the Tm is generally calculated as the product of $2\times(\Sigma+T)+4\times(\Sigma+C)$, wherein A is adenosine, T is thymidine, G is guanosine, and C is cytosine. For oligonucleotides greater than 20 nucleotides, the nearest-neighbor method was used and the Tm is calculated as the product of $(\Delta H/((A+\Delta S)+Rin\ (Ct/4)))(273.15)+16.6\ \log\ [salt]$, wherein $\Delta H$ (cal/mole) is the sum of the nearest-neighbor enthalpy changes for hybrid formation (<0), A (cal/K-mole) is a constant for helix initiation which is equal to −10.8 cal/K-mole for nonself-complementary sequences and −12.4 for self-complementary sequences, $\Delta S$ (cal/K-mole) is the sum of the nearest-neighbor entropy changes for hybrid formation (<0), R is the molar gas constant (1.987 cal/K-mole), [salt] is the molar salt concentration, and Ct is the total molar concentration of strands when oligonucleotides are not self-complementary or it is equal to 4 times this concentration in the case of self-complementary sequences. In the nearest neighbor formula the [salt] was fixed at 50 mM and the Ct was fixed at 250 pmole.

The above oligonucleotide PCR primer pair and oligonucleotide probe are specific to Campylobacter jejuni and do not cross-react with closely related members of the genera or unrelated members of the Enterobacteriaceae and do not amplify spurious unrelated nucleic acids. While the above oligonucleotide PCR primers and oligonucleotide probe are identified by particular nucleic acid sequences, the nucleic acid sequence of the oligonucleotide PCR primers or probe may be include nucleotides that are upstream or downstream of the particular nucleic acid sequence disclosed herein as long as the oligonucleotide PCR primers and oligonucleotide probe retain their specificity for Campylobacter jejuni and do not cross-react with closely related or unrelated members of the genera and do not amplify spurious unrelated nucleic acids.

In a typical identification reaction performed according to the present invention, a sample, containing either Campylobacter jejuni cells or DNA extracted from the cells, preferably the cells are at a concentration of about $10^{4-5}$ CFU/ml or about 10 ηg DNA, is added to a reaction mixture to provide a final reaction mixture containing 1.5 mM TAQMAN buffer, about 0.5 pmole each oligonucleotide PCR primer, about 0.2 to 0.8 mM each deoxynucleoside triphosphate (DNTP), about 0.2 μM of the oligonucleotide probe, about 2.5 units of a nucleic acid polymerase having 5' to 3' exonuclease activity and lacking 3' to 5' exonuclease activity, optionally 0.5 units AMPERASE (trademark of Perkin-Elmer), 4.5 mM MgCl$_2$, about 0.05% gelatin, and 0.01% TWEEN 20. The preferred volume for the final reaction mixture is 50 μl. Preferably, the nucleic acid polymerase is a TAQ DNA polymerase or equivalent thermal polymerase. The reaction is performed wherein the sample is denatured at about 95° C. for about 10 minutes, and annealed and extended at 60° C. for about 1 minute, followed by about 39 cycles of about 95° C. for about 30 seconds and 60° C. for 1 minute. After the last cycle the sample is cooled at 4° C. Optionally, the annealing can be at 5° C. for 1 minute and extension can be for 30 seconds at 72° C. Detection of fluorescence emissions released from exonuclease digested probe is monitored in real-time using an apparatus such as the ABI Prism 7700 sequence detector using 96-well reaction plates or GeneAmp PC System 9600 or 9700 in 9600 emulation mode followed by analysis in the ABA Prism Sequence Detector or TaqMan LS-50B PCR Detection System. The above are available from Perkin-Elmer Applied Biosystems. The amount of fluorescence detected is proportional to the amount of *Campylobacter jejuni* present in the environmental sample.

Using the above oligonucleotide PCR primers and the following dual-labeled oligonucleotide probes, the present invention further provides a method which distinguishes wild-type *Campylobacter jejuni* strains from mutant, antibiotic-resistant strains. The method, which is shown in FIG. 2, is an allelic discrimination method which can distinguish wild-type strains from ciprofloxacin-resistant strains of *Campylobacter jejuni*. The method is sensitive enough to distinguish sequences which differ by a single nucleotide change. Thus, the allelic discrimination as performed herein uses two oligonucleotide probes which target a nucleic acid sequence that differs in nucleotide sequence between the wild-type and the mutant antibiotic-resistant strain. Each oligonucleotide probe is labeled at the 5' end with a different energy transfer donor fluorophore, such as FAM at the 5' end of one probe and TET at the 5' end of the other probe and labeled at the 3' end with the same energy transfer acceptor or quenching fluorophore. Each donor fluorophore type fluoresces at a different wavelength, which enables them to be distinguished when released during the reaction. In the present invention, both oligonucleotide probes are complementary to the same target nucleic acid sequence of the QRDR of gyrA, i.e., complementary to the nucleic acid sequence of the QRDR that includes amino acid codon 86. The first oligonucleotide probe is complementary to the target nucleic acid sequence from wild-type strains, i.e., amino acid codon 86 encodes threonine, and the second oligonucleotide probe is complementary to the target nucleic acid sequence from mutant antibiotic-resistant strains, i.e., amino acid codon 86 encodes isoleucine. The two oligonucleotide probes compete for the target nucleic acid sequence and the genotype of the template is indicated by the relative fluorescence emission of the two donor fluorophores. The probes are particularly useful for distinguishing wild-type strains from ciprofloxacin-resistant strains of *Campylobacter jejuni*.

The wild-type oligonucleotide probe (TAQ2) and mutant oligonucleotide probe (TAQ3) were designed to distinguish between wild-type strains of *Campylobacter jejuni* and mutant strains resistant to high levels of the antibiotic ciprofloxacin. Both oligonucleotide probes anneal to the same region of the QRDR that contains amino acid codon 86 of gyrA. The probes are identical in sequence, except that probe TAQ3, which identifies the antibiotic-resistant strain, is a single nucleotide longer at the 3' end and is specific for the mutant isoleucine codon ATA at codon 86 whereas probe TAQ2, which identifies the wild-type strain, is specific for the threonine codon ACA at codon 86. The nucleotide sequence of TAQ2 is 5'-CCACATGGAGATACAGCAGTTTATGAT-3' (SEQ ID NO:6). TAQ2 is labeled at the 5' end with an energy transfer donor fluorophore and at the 3' end with an energy transfer acceptor fluorophore. Preferably, TAQ2 is labeled at the 5' end with the energy transfer donor fluorophore FAM and at the 3' end with the energy transfer acceptor fluorophore TAMRA. The nucleotide sequence of TAQ3 is 5'CCACATGGAGATATAGCAGTTTATGATGC-3' (SEQ ID NO:7). TAQ3 is labeled at the 5' end with an energy transfer donor fluorophore and at the 3' end with an energy transfer acceptor fluorophore. Preferably, TAQ3 is labeled at the 5' end with the energy transfer donor fluorophore TET and the 3' end with the energy transfer acceptor fluorophore TAMRA. Probe TAQ2 has a Tm of 58.9° C. and probe TAQ3 has a Tm of 59.2° C. The gyrA QRDR region that is complementary to TAQ2 and TAQ3 is highly conserved in *Campylobacter jejuni*. Only *Campylobacter jejuni* strain 49349 contained a mismatch with the nucleic acid sequences of these oligonucleotide probes. The mismatch was an A to G transition at nucleotide position 52 as shown in FIG. 3. The TAQ2 and TAQ3 oligonucleotide probes had approximately 86% identity with *Campylobacter coli* nucleic acid sequences. In a preferred embodiment, each oligonucleotide probe was phosphorylated at the 3' end in order to block chain extension of the oligonucleotide probe during PCR amplification.

In a typical allelic discrimination reaction performed according to the present invention, a sample, containing either *Campylobacter jejuni* cells or DNA extracted from the cells, preferably the cells are at a concentration of about $10^{4-5}$ CFU/ml or DNA at a concentration of about 10 ηg DNA, is added to a reaction mixture to provide a reaction mixture containing 1.5 mM TAQMAN buffer, about 0.5 pmole each oligonucleotide PCR primer, about 0.2 to 0.8 mM each deoxynucleoside triphosphate (dNTP), about 0.2 $\mu$M each of wild-type oligonucleotide probe and mutant oligonucleotide probe, about 2.5 units of a nucleic acid polymerase having 5' to 3' exonuclease activity and lacking 3' to 5' exonuclease activity, optionally 0.5 units AMPERASE, 4.5 mM $MgCl_2$, about 0.05% gelatin, and 0.01% TWEEN 20. The preferred volume for the reaction mixture is 50 $\mu$l. Preferably, the nucleic acid polymerase is a TAQ DNA polymerase or equivalent. The reaction is performed wherein the sample is denatured at about 95° C. for about 10 minutes, and annealed and extended at 60° C. for about 1 minute, followed by about 39 cycles of about 95° C. for about 30 seconds and 60° C. for 1 minute. After the last cycle the sample is cooled at 4° C. until removed. Optionally, the annealing can be at 50° C. for 1 minute and extension can be for 30 seconds at 72° C. Detection of fluorescence emissions is monitored in real-time using a apparatus such as an ABI Prism 7700 Sequence Detection System available from Perkin-Elmer Applied Biosystems. The amount of fluorescence detected from each probe is proportional to the amount of wild-type to antibiotic-resistant *Campylobacter jejuni* present in the environmental sample.

In the prior art, the general method for isolation and identification of *Campylobacter jejuni* entails a pre-enrichment step wherein the sample is placed in supplement broth and incubated for 24–48 hours under suitable growth conditions. This is followed by an isolation step that entails subculturing the culture from the pre-enrichment step onto Campylobacter selective media and incubation for an additional 48 to 72 hours. The identity of isolated colonies of Campylobacter from the selective media can be confirmed using biochemical tests or PCR. Antibiotic susceptibility testing can be done afterwards and takes at least 24 hours to perform. Therefore, using prior art methods, it can take anywhere from 3 to 5 days to determine whether a sample contains *Campylobacter jejuni*. Even if the sample is identified to contain *Campylobacter jejuni*, the process of culturing and subculturing the isolated Campylobacter renders it impossible to determine the amount of Campylobacter in the sample. In the case of determining whether the *Campylobacter jejuni* is resistant to an antibiotic, it can take an additional day or more to determine whether the *Campylobacter jejuni* is resistant to an antibiotic. Like the detection method, it is not possible to determine the proportion of antibiotic-resistant to antibiotic-susceptible *Campylobacter jejuni*.

The present invention is an improvement over the prior art because an environmental sample can be analyzed directly. Either the cells in the environmental sample are analyzed directly in the PCR reaction of the present invention because the cells will lyse under the PCR reaction conditions, thereby releasing their DNA, or the cells are lysed before the PCR reaction according to methods well known in the art and the DNA, which is released from the lysed cells sample, are analyzed according to the present invention, or purified DNA is isolated from the cells by methods well known in the art and a portion of the isolated DNA is used in the PCR reaction of the present invention.

However, when the concentration of *Campylobacter jejuni* in an environmental sample is very low or the environmental sample contains compounds which are inhibitors of the PCR reaction, an enrichment step that precedes the PCR reaction is appropriate. For example, about 100 to 1000 *Campylobacter jejuni* organisms should be in the sample in order to detect the fluorescence that is produced during the PCR reaction. This is about 10 to 100-fold less than the number of organisms needed to detect amplified product by agarose gel electrophoresis. Thus, if a sample contained only a single organism or an inhibitor that reduced the efficiency of the PCR reaction, either insufficient detectable fluorescence would be produced during the process, which would limit the sensitivity of the process, or the fluorescence would be erratic with the intensity of fluorescence varying from sample to sample, which would limit the reliability of the process. Furthermore, it is well known that particular samples, e.g., urine and fecal samples, contain inhibitors which inhibit the polymerase used in the PCR reaction. Therefore, in order to enhance the sensitivity and reliability of the process of the present invention, the present invention further includes the following embodiments for enhancing the sensitivity of the process.

In one embodiment, the environmental sample is incubated in supplement broth for 24–48 hours under suitable growth conditions. Following the incubation, an aliquot of cells is directly analyzed according to the present invention or DNA is isolated from the cells in the aliquot and the DNA is analyzed according to the present invention. This enrichment step enables any *Campylobacter jejuni* in the sample to grow, thus providing a sufficient amount of cells which enables extraction of a sufficient quantity of nucleic acid to be analyzed according to the process of the present invention. The enrichment also dilutes the concentration of any inhibitors in the environmental sample. A suitable enrichment step is to grow the microorganisms in an environmental sample in a culture consisting of Brucella broth supplemented with 5% defibrinated sheep blood at 37° C. in 5% $CO_2$ for 24 to 48 hours, harvest the cells in the culture, and extract the chromosomal DNA using standard DNA extraction methods. A sample of the extracted DNA is then analyzed in the process of the present invention.

In another embodiment, which enhances the sensitivity of the analysis, the cells or DNA isolated from the cells in the environmental sample are preamplified in a PCR reaction using primers JL 223 and JL 224 which were described in (Husmann et al., J. Clin. Microbiol. 35: 2398–2400 (1987)). These primers amplify a 433 bp fragment containing the entire QRDR in strains of *Campylobacter jejuni, Campylobacter coli*, and *Campylobacter fetus*. Primer JL 223 has the nucleotide sequence 5'-CGCCATACCTACAGCTATACC-3' (SEQ ID NO:8) and primer JL 224 has the nucleotide sequence 5'-GATGGTTTAAAGCCTGTTCAT-3' (SEQ ID NO:9). The PCR reaction preferably contains about 0.2 mM each DNTP, 0.5 pmole per μl each primer, about 2 mM $Mg^{2+}$ and 0.05 units per μl DNA polymerase. The PCR reaction is performed as follows: 1 minute at 94° C., then 1 minute at 50° C., and then 30 seconds at 72° C. The preferred reaction volume is about 50 μl. The PCR reaction is performed for about 32 to 39 cycles. After this PCR reaction, which amplifies the QRDR from Campylobacter spp., an aliquot of the PCR reaction is then subjected to the above identification or allelic discrimination assay, which amplifies only the wild-type or mutant QRDR portion of the amplified QRDR. This embodiment enhances the sensitivity when the environmental sample contains an amount of *Campylobacter jejuni* which may not be detectable without first performing the above pre-amplification step, e.g., a large sample volume wherein the number of *Campylobacter jejuni* organisms would not expected to contain more than 1 microorganism per sample. Alternatively, the first PCR reaction is performed using primers JL 238 and JL 239.

In an embodiment further still of the present invention, the environmental sample is subjected to an immunomagnetic separation step in which magnetic beads coated with antibodies against *Campylobacter jejuni* are used to collect the *Campylobacter jejuni* from the environmental sample free of other organisms and inhibitors. The immunomagnetic separation embodiment is used to separate and/or concentrate *Campylobacter jejuni* from environmental sources which include, but are not limited to, water, stool, feed, food, environmental swab, and animal feces. Because the immunomagnetic separation embodiment avoids the need to culture the *Campylobacter jejuni* prior to the above PCR reactions, the immunomagnetic separation step is useful for concentrating the *Campylobacter jejuni* in a sample, particularly when the concentration of *Campylobacter jejuni* in the sample is insufficient to provide sufficient DNA for PCR analysis. Thus, the immunomagnetic separation step reduces the amount of time necessary to identify antibiotic-resistant *Campylobacter jejuni* because it reduces the need to enrich the sample for *Campylobacter jejuni* by sub-culturing. Importantly, the immunomagnetic embodiment method enables the "actual" or "real" amount of *Campylobacter jejuni* in an environmental sample be determined. Also important is that the immunomagnetic embodiment enables a sufficient amount of cells to be obtained from an environmental sample for the allelic discrimination assays wherein the proportion of antibiotic-resistant to antibiotic-susceptible *Campylobacter jejuni* is similar to the proportion in the environmental sample.

In general, antibodies which are specific for *Campylobacter jejuni* are attached to super-paramagnetic mono-sized polymer particles to make immunomagnetic beads. The immunomagnetic beads are mixed with an environmental sample and the immunomagnetic beads complexed with *Campylobacter jejuni* in the sample are separated from the sample by a magnetic field. There are two ways to separate *Campylobacter jejuni* using immunomagnetic separation, positive isolation and negative isolation.

In the positive isolation embodiment, the paramagnetic beads are coated with anti-*Campylobacter jejuni* antibodies and the coated beads mixed with the environmental sample. The beads complex with *Campylobacter jejuni* in the sample, and the complexes are removed by a magnetic field. In an indirect embodiment of the positive isolation embodiment, the anti-*Campylobacter jejuni* antibodies are mixed with the environmental sample wherein the antibodies bind the *Campylobacter jejuni* in the sample to form a first complex. The first complex is separated from the sample by adding to the mixture paramagnetic beads coated with an antibody against the anti-*Campylobacter jejuni* antibodies. The immunomagnetic beads binds the first complex forming a second complex which is separated from the sample by a magnetic field. The *Campylobacter jejuni* is eluted from the immunomagnetic beads in sterile water and analyzed as taught herein.

In a negative isolation embodiment, unwanted cells are removed from the sample by providing a cocktail comprising antibodies against a variety of unwanted cells. The antibodies bind to the unwanted cells. Next, the immunomagnetic beads coated with an antibody against the antibodies in the cocktail are added which binds all of the antibodies, including those bound to the cells. The bound cells are separated by a magnetic field. The *Campylobacter jejuni*, which remains in the sample, is analyzed as taught herein.

Preferably, the immunomagnetic separation uses the positive isolation method and the antibody against *Campylobacter jejuni* is a monoclonal antibody such as #1744–9006, which is commercially available from Biogenesis. The monoclonal antibody is against a soluble antigen that is bound to the outer surface of *Campylobacter jejuni*. The monoclonal antibody reacts against several species of Campylobacter. Immunomagnetic beads containing anti-mouse IgG are resuspended thoroughly in the vial and the desired amount of beads transferred to a tube. Preferably, 25 $\mu$l of $10^7$ beads per ml is transferred to the tube. The tube is placed in a magnetic block and the fluid is removed. The beads are washed twice with washing buffer (phosphate buffered saline (PBS) containing 1% bovine serum albumen (BSA)). Next, the beads are incubated with mouse anti-*Campylobacter jejuni* monoclonal antibodies (Biogenesis #1744–9006) in washing buffer at about 1 $\mu$g of antibodies for every $10^7$ beads. The antibodies are bound to the beads by incubating for about 2 hours at 40° C. with gentle mixing. Afterwards, the tube containing the antibody-complexed beads are placed in a magnetic block and washed twice with washing buffer. The beads are resuspended in about 25 $\mu$l of washing buffer. An environmental sample is cooled to 4° C. and added to the beads and incubated for about 1 hour at 4° C. with gentle mixing. Afterwards, the tube is placed in a magnetic block for about 2 minutes to allow separation. The fluid is removed, the beads removed from the magnetic block and washed with washing buffer. The tube is returned to the magnetic block and after about 1 minute, the fluid is removed. The washing is repeated at least once. Then, any bound *Campylobacter jejuni* is eluted from the beads with sterile water. Afterwards, the tube is placed in the magnetic block and the sterile water containing the *Campylobacter jejuni* is transferred to another tube. The *Campylobacter jejuni* is then analyzed according to the PCR detection method of the present invention.

Thus, the present invention, which includes the immunomagnetic separation, saves time and enables the "real" or "actual" amount of *Campylobacter jejuni* in an environmental sample to be determined. The present invention further enables the "actual" proportion of antibiotic-resistant to antibiotic-susceptible *Campylobacter jejuni* to be determined in an environmental sample.

Finally, while the above primers and probes are preferably used in a TAQMAN-based assay, the present invention further provides for the identification of *Campylobacter jejuni* in an environmental sample in a PCR reaction that uses the primers as taught above but wherein the PCR products are identified by agarose gel electrophoresis. Identification of antibiotic-resistant strains can be accomplished by Southern transfers of the agarose gels and probing the transfers with labeled TAQ2 and/or TAQ3 probes to determine whether the sample contains strains which are antibiotic resistant. Southern transfers and making and using labeled probes that detect nucleic acids on Southern transfers are well known in the art.

The following examples are intended to promote a further understanding of the present invention.

EXAMPLE 1

In this example, sequence analysis of the QRDRs of several Campylobacter isolates was performed which enabled the design of *Campylobacter jejuni* specific PCR primers and dual labeled probes. These primers and probes were then used to develop a TAQMAN assay which detects femtogram amounts of Campylobacter chromosomal DNA. The allelic discrimination embodiment assay of the present invention was used to distinguish between wild-type strains and mutant strains resistant to high levels of ciprofloxacin. Sequence analysis was also shown to effectively identify Campylobacter isolates to the species levels.

TABLE 1

| Species | Strain | Source | Institution/Reference | $C_T$for $\Delta R_c = 0.2$[e] | Allelic Discrimination[f] |
|---|---|---|---|---|---|
| *Aeromoras salmonicida*[a] | 214889 | Salmon | Oppegamil and Sorum, 1996 | | |
| *Enterobacter cloacae* | 23355 | Human | ATCC | $\Delta R_c < 0.2$ after 40 cycles | |
| *Erwinia carotovora*[a] | | | Rosanes et al, 1994 | | |
| *Escherichia coli* | 25922 | Human | ATCC | $\Delta R_c < 0.2$ after 40 cycles | |
| *E. coli*[a] | H560 | | Swanberg and Wang, 1987 | | |
| *Campylobacter jejuri* | 15046764 | Bovine | MSU Vetrinary College | | |
| *C. jejuni*[b] | 15046764 CR216-1 | Bovine | This study | 16.3, 16.4 | Allele 1 |
| *C. jejuni* | 19084571 | Ovine | MSU Vetrinary College | 15.8, 15.8 | Allele 2 |
| *C. jejuni* | 19094451 | Ovine | MSU Vetrinary College | | |
| *C. jejuni* | 197985544 | Canine | MSU Vetrinary College | 15.8, 15.7 | Allele 2 |
| *C. jejuni* | 4300 | Human | M. Konkel (Wash. State Univ) | 16.9, 16.0 | Allele 2 |
| *C. jejuni*[b] | 4300 CR216-1 | Human | This study | | Allele 1 |
| *C. jejuni* | 4132958 | Human | M. Konkel (Wash. State Univ) | 16.0, 16.0 | Allele 2 |
| *C. jejuni*[b] | 4132958 CR216-1 | Human | This study | | Allele 1 |

TABLE 1-continued

| Species | Strain | Source | Institution/Reference | $C_T$ for $\Delta R_c = 0.2$[e] | Allelic Discrimination[f] |
|---|---|---|---|---|---|
| C. jejuni | 4239928 | Human | M. Konkel (Wash. State Univ) | 16.1, 16.1 | Allele 2 |
| C. jejuni | E961009 | Human | M. Konkel (Wash. State Univ) | 15.8, 15.9 | |
| C. jejuni | E972653 | Human | M. Konkel (Wash. State Univ) | | |
| C. jejuni | E972796 | Human | M. Konkel (Wash. State Univ) | 16.2, 16.4 | |
| C. jejuni[b] | E972796 CR216-1 | Human | This study | | Allele 1 |
| C. jejuni | E9795412 | Human | M. Konkel (Wash. State Univ) | 16.1, 16.1 | |
| C. jejuni | 81176 | Human | C. Pickett (Univ. of Kentucky) | 16.5, 16.5 | Allele 2 |
| C. jejuni[b] | 81176 CR216-1 | Human | This study | | Allele 1 |
| C. jejuni | 3124 | | USDA | 16.4, 16.2 | Allele 2 |
| C. jejuni | 3128 | Human | USDA | | |
| C. jejuni | 3130 | Chicken | USDA | | |
| C. jejuni[b] | 3130 CR216-1 | Chicken | This study | | |
| C. jejuni | 3131 | Chicken | USDA | 16.7, 16.6 | |
| C. jejuni | 3133 | Bovine | USDA | | |
| C. jejuni | 3136 | Human | USDA | | |
| C. jejuni | 3383 | | USDA | | |
| C. jejuni | 33291 | Human | ATCC | 17.0, 16.9 | |
| C. jejuni[b] | 33291 CR216-1 | Human | This study | | |
| C. jejuni | 33292 | Human | ATCC | | |
| C. jejuni[b] | 33292 CR216-2 | Human | This study | | |
| C. jejuni | 33560 | Bovine | ATCC | 15.0, 14.9 | Allele 2 |
| C. jejuni[b] | 33560 CR2 | Bovine | This study | | |
| C. jejuni[b] | 33560 CR6 | Bovine | This study | | |
| C. jejuni | 43429 | Human | ATCC | | |
| C. jejuni[b] | 43429 CR216-1 | Human | This study | | |
| C. jejuni | 43430 | Bovine | ATCC | | |
| C. jejuni | 43433 | Human | ATCC | 16.0, 15.9 | Allele 2 |
| C. jejuni | 43470 | Human | ATCC | | |
| C. jejuni[b] | 43470 CR216-1 | Human | This study | 15.8, 16.0 | Allele 1 |
| C. jejuni[c] | 49349 | Human | ATCC | 16.3, 16.3 | Allele 2 |
| C. jejuni[a] | UA580 | | Wang et al, 1993 | | |
| C. coli | 550 | Porcine | MSU Veterinary College | | |
| C. coli | 1935 | Porcine | MSU Veterinary College | | |
| C. coli | 18493 | Porcine | MSU Veterinary College | | |
| C. coli | 1679368 | Monkey | MSU Veterinary College | | No significant amplification |
| C. coli | 1714086 | Porcine | MSU Veterinary College | | |
| C. coli | 1777708 | Porcine | MSU Veterinary College | | No significant amplification |
| C. coli | 1798888 | Porcine | MSU Veterinary College | | |
| C. coli | 1808517 | Porcine | MSU Veterinary College | | |
| C. coli | 17010887 | Porcine | MSU Veterinary College | | |
| C. coli | 17977081 | Porcine | MSU Veterinary College | | |
| C. coli | 3118 | Porcine | USDA | $\Delta R_c < 0.2$ after 40 cycles | No significant amplification |
| C. coli | 3119 | Chicken | USDA | $\Delta R_c < 0.2$ after 40 cycles | No significant amplification |
| C. coli | 3120 | Human | USDA | | |
| C. coli | 3132 | Chicken | USDA | | |
| C. coli | 3135 | Oyster | USDA | | |
| C. coli | 3384 | | USDA | $\Delta R_c < 0.2$ after 40 cycles | No significant amplification |
| C. coli | 3386 | | USDA | $\Delta R_c < 0.2$ after 40 cycles | No significant amplification |
| C. coli | 33599 | Porcine | ATCC | | |
| C. coli | 43134 | Porcine | ATCC | $\Delta R_c < 0.2$ after 40 cycles | |
| C. coli | 43473 | Human | ATCC | $\Delta R_c < 0.2$ after 40 cycles | |
| C. coli | 43474 | Human | ATCC | | |
| C. coli | 43479 | Human | ATCC | | |
| C. coli | 43482 | Human | ATCC | | |
| C. coli[a] | 11366 | | NCTC/Genbank U63413 | | |
| C. fetus | 27374 | Ovine | ATCC | | No significant amplification |
| C. hyoilei[d] | 51729 | Porcine | ATCC | | No significant amplification |
| C. lari | 43675 | Human | ATCC | $\Delta R_c < 0.2$ after 40 cycles | |
| C. lari | 3121 | Chicken | USDA | | |
| C. lari[a] | 35221 | Gull | ATCC/Genbank U63412 | | |
| C. upsaliensis | 43954 | Canine | ATCC | | No significant amplification |
| Hebcobacter pylari[a] | UC946 | Human | Moore et al., 1995 | | |
| Klebsiella pneumoniae[a] | M5A1 | | Dimari and Das, 1990 | | |
| Pseudomonas aeruginosa[a] | PAO1 | | Kurcishi et al., 1994 | | |

[a]The DNA sequences of these strains were acquired from Genbank.
[b]Ciprofloxacin-resistant isolates that contains a C→T transition in codon 86 of gyrA
[c]Subspecies doylei.
[d]Recently reclassified as a C. coli species (33).
[e]Duplicat analysis TaqMan assay with TAQ1 probe and 10 ng chromosomal DNA per reaction.
[f]Duplicate analysis Allelic Discrimination assay with TAQ2 and TAQ3 probes.
An allele 1 (ciprofloxacin-resistant mutant) sample is characterized by an allele 1-specific signal (TET) greater than 0.90 units and an allele 2-specific signal (FAM) less than 0.10 units.
An allele 2 (wild-type) sample is characterized by an allele 1-specific signal less than 0.25 units and an allele 2-specific signal greater than 0.75 units.
Used 10 ng chromosomal DNA per reaction.

The Campylobacter strains that were used are listed in Table 1. Strain identification was confirmed either with the API CAMPY system (Biomerieux, France), or in collaboration with the diagnostic laboratory at the Michigan Department of Community Health in Lansing Michigan using NCCLS guidelines. Bacteria were grown on Brucella Agar (BBL Microbiology Systems, Becton Dickinson, Cockeysville, Maryland) supplemented with 5% defibrinated sheep blood (Cleveland Scientific, Bath, Ohio), herein referred to as BASB medium, at 37° C., in 5% $CO_2$, for 36 to 48 hours. After growth, the cells were harvested and suspended in Brucella broth for chromosomal extraction as set forth below.

For isolation of ciprofloxacin-resistant *Campylobacter jejuni* mutants, bacterial cultures were grown as above and then resuspended in Brucella broth to a concentration of about $10^{10}$ colony forming units (CFU) per ml. Cultures were then plated onto BASB agar containing ciprofloxacin (Bayer Corporation, Kankakee, Ill.) at a concentration of 2 or 16 $\mu$g per ml.

Ciprofloxacin-resistant mutants were passaged on BASB agar plates containing ciprofloxacin at a concentration of 16 $\mu$g per ml to confirm the resistant phenotype. Chromosomal DNA samples of these mutants were sequenced as set forth below and the presence of the C to T transition in amino acid codon 86 of gyrA was confirmed for each mutant isolated.

For isolating DNA, the bacterial cultures were pelleted and the DNA extracted using standard methods (Ausubel et al., In *Current Protocols in Molecular Biology*. John Wiley & Sons, Inc., New York, N.Y.). Briefly, the cells were resuspended in TE buffer (10 mM Tris-HCl, 1 mM EDTA [pH 8.0]) and lysed with 0.5% sodium dodecylsulfate (SDS) in the presence of 100 $\mu$g/ml proteinase K. Cellular debris was removed by complexing with hexadecyltrimethyl ammonium bromide followed by phenol/chloroform extraction and RNase A digestion. The DNA was then precipitated with 0.6× volume of isopropanol, redissolved in TE buffer and quantified using a DU 530 spectrophotometer (Beckman Instruments, Schaumberg, Ill.).

The QRDR, which is about 400 bp, was amplified from each Campylobacter strain using primers JL 223 and JL 224 which were described in (Husmann et al., J. Clin. Microbiol. 35: 2398-2400 (1987)). These primers amplify a 433 bp fragment containing the entire QRDR in strains of *Campylobacter jejuni, Campylobacter coli*, and Campylobacter fetus. Primers JL 297 and JL 299 were designed for the PCR amplification of the corresponding gyrA region in *E. coli*. The *E. coli* primer set was also used for amplification of Enterobacter chromosomal DNA. The concentration of reagents in these PCR reactions were as follows: 2–4 ηg/$\mu$l DNA, 0.2 mM each DNTP, 0.5 pmole/$\mu$l each primer, approximately 2 mM $Mg^{2+}$ and 0.05 U/$\mu$l Pfu DNA polymerase (available from Stratagene, La Jolla, Calif.). The PCR reaction was carried through 32 cycles wherein each cycle consisted of 1 minute at 94° C. for denaturing, 1 minute at 50° C. for annealing, and 30 seconds at 72° C. for extension. Afterwards, the amplified DNA was separated by gel electrophoresis using a 1.75% low-melting temperature agarose gel (SEAPLAQUE GTG available from FMC Bioproducts, Rockland, Me.) and the DNA purified by cutting the DNA out of the gel and purifying the DNA using a QIAQUICK gel extraction kit (available from Qiagen, Valencia, Calif.). The DNA was then sequenced in the Michigan State University Sequencing Facility using the dye terminator cycle sequencing method which used the JL 297 and JL 299 primers and the ABI 377 DNA sequencer (Perkin-Elmer Applied Biosystems, Foster City, Calif.).

Using forward and reverse primers for cycle sequencing, sequence data was obtained for 28 wild-type *Campylobacter jejuni* isolates and 12 Campylobacter mutants able to grow on BASB medium containing ciprofloxacin at a concentration of 16 $\mu$g/ml. The DNA sequences were analyzed using the Pileup and GrowTree programs of Genetics Computer Group (Madison, Wis.) SeqWeb software. Multiple sequence alignment and phylogram analysis of the amplified Campylobacter QRDRs are shown in FIGS. 3 and 4, respectively.

The sequence alignments allowed for the design of primers and probes for the method of the present invention: primer JL 238, primer JL 239, probe TAQ1, probe TAQ2, and probe TAQ3. With each probe, the FAM or TET energy transfer donor fluorophore (donor reporter dye) was attached to the 5' nucleotide and the TAMRA energy transfer acceptor fluorophore (quencher) was positioned at the 3' nucleotide. Each probe was phosphorylated at the 3' end in order to prevent extension of the probes during PCR amplification. The primers were made by Integrated DNA Technologies, Coralville, Iowa.

The sequence for primer JL 238 was selected because it showed 100% identity to 27 of 28 *Campylobacter jejuni* strains analyzed. *Campylobacter jejuni* E961009 was the single exception; it contained only a one base mismatch (95% identity) with primer JL 238. Similarly, the JL 239 primer was designed for its 100% identity with all *Campylobacter jejuni* sequences analyzed. The specificity of these primers is sufficient to distinguish between isolates of *Campylobacter jejuni* and other bacterial species examined by standard PCR methods as shown in FIG. 5, which shows that the primers amplify the expected 192 bp PCR product from *Campylobacter jejuni* isolates but not from other Campylobacter spp. The positioning of the JL 238 and JL 239 primers to target the sequence containing amino acid codon 86 was also important for the development of the allelic discrimination assay (shown in FIG. 3).

Probe TAQ1 was designed for the purpose of *Campylobacter jejuni* identification and was, therefore, localized to a region between JL 238 and JL 239 which was 100% conserved among all *Campylobacter jejuni* isolates. It was not necessary for this probe to distinguish between different species of Campylobacter because primers JL 238 and JL 239 served this purpose. However, it was necessary for the probe to anneal to all Campylobacter gyrA QRDR DNA and to have a Tm similar to the Tms for JL 238 and JL 239. Probe TAQ1 did show identity with *Campylobacter coli* DNA ranging from 88 to 92%.

Probe TAQ2 and probe TAQ3 were designed to distinguish between wild-type strains of *Campylobacter jejuni* and those resistant to high levels of ciprofloxacin. Both probes annealed to a region of QRDR DNA containing amino acid codon 86 of gyrA. The probes are identical in sequence, except that probe TAQ3 is a single nucleotide longer at the 3' end and is specific for the mutant isoleucine codon ATA at codon 86 whereas probe TAQ2 is specific for the wild-type threonine codon ACA at codon 86. The *Campylobacter jejuni* isolates analyzed herein were highly conserved in the chromosomal region where probes TAQ2 and TAQ3 specifically annealed. Only *Campylobacter jejuni* strain cj49349 contained a mismatch with these probe sequences. This was an A to G transition at nucleotide position 52 as shown in FIG. 3. The TAQ2 and TAQ3 probes had approximately 86% identity with *Campylobacter coli* sequences. The probes and primers have Tms similar to each other.

EXAMPLE 2

This example shows the ability of the detection assay of the present invention to identify chromosomal DNA from

*Campylobacter jejuni* using the TAQMAN assay and primers JL 238 and JL 239 and probe TAQ1.

The TAQMAN PCR reaction mixture concentrations were as follows: 1× TAQMAN buffer (available from Perkin-Elmer Applied Biosystems, Foster City, Calif.), 0.2 mM each dNTP (0.4 mM dUTP), 0.5 pmole per µl each primer, 200 ηM TAQ1, 0.05 units per µl AMPLITAQ Gold polymerase (Perkin-Elmer Applied Biosystems), 0.01 units per µl AMPERASE UNG (Perkin-Elmer Applied Biosystems), 4.5 mM $MgCl_2$, 0.05% gelatin, and 0.01% TWEEN 20.

After an initial denaturation step at 95° C. for 10 minutes, the following cycle was repeated 40 times: 60° C. for 1 minute, followed by 95° C. for 30 seconds. Prior to the initial denaturation, all TAQMAN reactions were incubated at 50° C. for two minutes in the presence of AMPERASE UNG in an effort to prevent PCR product carryover. Detection of fluorescence emissions were monitored in real-time with an ABI Prism 7700 Sequence Detection System (Perkin-Elmer Applied Biosystems). DNA standards were prepared using *Campylobacter jejuni* chromosomal DNA serially diluted in reverse osmosis deionized water. The Passive Reference Dye used for normalization of reporter fluor signal was included in the TAQMAN reaction buffer.

The results of two of the above assays are shown in FIG. 6. The results were reported as ΔRn vs. PCR cycle, wherein ΔRn is the difference in normalized reporter fluor signal between a PCR tube with sample DNA and a no DNA control. The threshold level (defined in ΔRn units), which is used to indicate a positive reaction, was adjusted to enhance the linear relationship between DNA mass and threshold cycle. The fluorescence level of the no DNA controls should not exceed the threshold and are the basis for determining an appropriate threshold level. Using a threshold setting of 0.2 fluorescence units, and an initial quantity of 10 ηg of chromosomal DNA, which is roughly equivalent to $10^7$ genomes of *Campylobacter jejuni* (Waegel and Nachamkin, Molec. and Cell. Probes 10: 75–80 (1996)), a positive reaction identifying the DNA to be of *Campylobacter jejuni* origin was indicated before 18 PCR cycles in both assays. FIG. 7 shows that the relationship between the PCR cycle at which a particular DNA sample reaches threshold and the initial quantity of that DNA is approximately linear over at least seven logs of DNA mass measurement, ranging from 10 ηg to 10 femtograms ($10^{-15}$ g). Thus, a one femtogram *Campylobacter jejuni* DNA sample could be detected by 40 PCR cycles; however, this level of detection was inconsistent. As shown in FIG. 6, 10 ηg chromosomal DNA samples of *Campylobacter coli* cc43473 and *Campylobacter coli* cc43134 failed to achieve a threshold level of fluorescence after 40 PCR cycles. Chromosomal samples of strains directly tested according to the present invention and the results are shown in Table 1.

The results demonstrate that the detection assay of the present invention can detect one femtogram of chromosomal DNA which is about equivalent to a single *Campylobacter jejuni* genome, and can repeatedly detect 10 femtograms of chromosomal DNA.

The detection assay monitors amplification of the PCR product in real-time, thus eliminating the necessity for gel electrophoresis in diagnostic settings. Because of the linear relationship between initial DNA mass and the PCR threshold cycle, the assay is also quantitative for *Campylobacter jejuni* in an environmental sample.

EXAMPLE 3

This example shows the ability of the allelic discrimination assay of the present invention to distinguish chromosomal DNA from ciprofloxacin-resistant strains of *Campylobacter jejuni* from chromosomal DNA from ciprofloxacin-susceptible strains of *Campylobacter jejuni* using the TAQMAN assay and primers JL 238 and JL 239 and TAQ2 and the TAQ3 probes.

For discrimination between wild-type and high-level ciprofloxacin-resistant *Campylobacter jejuni* strains, primers JL 238 and JL 239 were used in combination with TAQ2 and TAQ3. The TAQMAN PCR reaction mixture concentrations and reaction conditions were the same as those in Example 2 with the exception that both TAQ2 and TAQ3 were included in the reaction mixture, each at a concentration of 200 ηM. Chromosomal DNA from either *Campylobacter jejuni* cj33560cr6 or *Campylobacter jejuni* cj33292cr2162, ciprofloxacin-resistant isolates, was used in the allele 1 standard reactions. Chromosomal DNA from either *Campylobacter jejuni* cj33292 or *Campylobacter jejuni* cj33560, wild-type isolates, was used in the allele 2 standard reactions. All allelic discrimination assays, with the exception of the controls that did not contain DNA, contained 10 ηg of chromosomal DNA. The allelic discrimination standards were prepared according to the specifications of Applied Biosystems.

Figure 9:
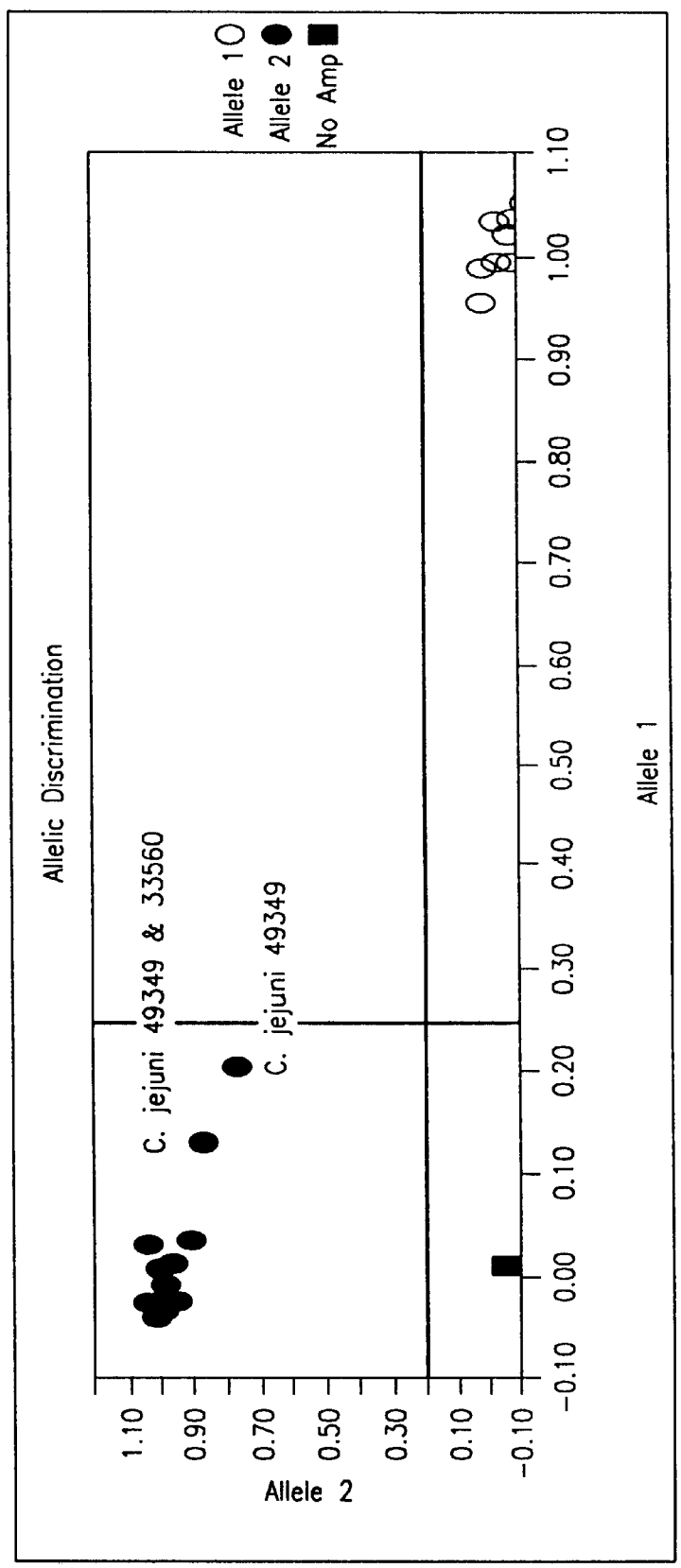
FIG. 9 shows determination of a ciprofloxacin-resistant or wild-type genotype by the allelic discrimination method of the present invention. Red circles represent allele 1 chromosomal samples from ciprofloxacin-resistant strains. The blue circles represent allele 2 chromosomal samples from wild-type strains. *Campylobacter coli* and no DNA controls are indicated by black squares. Eight standards representing an allele 1 fluorescent emission pattern and eight standards representing an allele 2 emission pattern are also shown.

The results are shown in FIGS. 8 and 9. Allelic discrimination is an endpoint assay where reporter fluor emissions, after the PCR cycle, are used to indicate the sample contains a ciprofloxacin-resistant *Campylobacter jejuni* strain or a ciprofloxacin-susceptible strain of *Campylobacter jejuni*. A no DNA template control, an allele 1 specific standard reaction, and an allele 2 specific standard reaction were always included with each assay in order to obtain fluorescent spectra for each type of reaction. The spectra of unknown chromosomal samples were compared to these reference reactions, and detection system algorithms were used to assign a value from approximately zero to one unit for the contribution of each allele-specific signal to the reaction spectra. Based on these values, unknown DNA samples were identified as either containing DNA from a ciprofloxacin-resistant strain of *Campylobacter jejuni*, DNA from a ciprofloxacin-susceptible strain of *Campylobacter jejuni*, or no *Campylobacter jejuni* DNA at all.

In FIG. 8, the FAM and TET emissions are shown in real-time from PCR samples of three *Campylobacter jejuni* isolates. Strains cj33560 and cj49349 are wild-type and strain cj33292cr216 is an isolate resistant to high levels of ciprofloxacin. As shown, strain 33560 produced the greatest FAM signal at PCR cycle 40. The chromosomal sequence of this strain possessed a 100% match with the sequence of probe TAQ2 (complementary to wild-type QRDR DNA). Isolate cj33292cr2162 produced the lowest FAM signal because of the mismatch between TAQ2 sequence and isolate cj33292cr2162 sequence at amino acid codon 86. A comparison of TET signals in the same reaction showed that strain cj33292cr2162, which has 100% sequence identity with probe TAQ3, which contains the C to T transition at amino acid codon 86 that confers ciprofloxacin resistance, had the highest TET signal and strain 33560, which has the wild-type amino acid codon 86, had the lower TET signal.

*Campylobacter jejuni* cj49349 was chosen for an analysis because it was the only strain in the collection which had an undesirable mismatch with both TAQ2 and TAQ3 (an A to G transition at nucleotide position 52 as shown in FIG. 3). Similar to wild-type strain cj33560, strain cj49349 also contains a mismatch at amino acid codon 86 with TAQ3. As shown in FIG. 9, despite the mismatch in the 5' region of both probes, strain 49349 was qualified as wild-type. With respect to antibiotic susceptibility, strain cj49349 was unable to grow on BASB agar supplemented with ciprofloxacin at 16 µg per ml.

The allelic discrimination assay as shown in FIG. 9 demonstrates that samples of wild-type strains of *Campylobacter jejuni* DNA and allele 2 standard reactions all possess an allele 2-specific signal greater than 0.75 units and an allele 1-specific signal less than 0.25 units. The samples of ciprofloxacin resistant chromosomal DNA and allele 1 standard reactions created an allele 1-specific signal greater than 0.90 units and an allele 2-specific signal less than 0.10 units. The resistant and susceptible genotypes were clearly identified as shown by the groupings in FIG. 9. Also run in the assay were samples of *Campylobacter coli* cc1777708 chromosomal DNA. The reactions containing these samples and the no DNA controls all produced allele 1- and allele 2-specific signals of less than 0.05 units. The results of chromosomal samples from strains that were directly tested by the allelic discrimination assay of the present invention are shown in Table 1. These results demonstrate that the allelic discrimination assay of the present invention not only identifies *Campylobacter jejuni* but to also distinguishes ciprofloxacin-resistant strains from ciprofloxacin-susceptible strains.

EXAMPLE 4

This example shows separation of *Campylobacter jejuni* from an environmental sample using the following immunomagnetic separation method.

Dynabeads pan mouse IgG (Dynal, Inc. #110.21) were resuspended thoroughly in their storage vial and the desired amount of beads transferred to a tube. 25 $\mu$l of $10^7$ beads per ml was transferred. The tube was placed in a magnetic block (Home Depot) and the fluid was removed. The beads were washed twice with washing buffer (phosphate buffered saline (PBS) containing 1% bovine serum albumen (BSA)). Next, the beads were incubated with mouse anti-*Campylobacter jejuni* monoclonal antibodies (Biogenesis #1744-9006) in washing buffer at 1 $\mu$g of antibodies for every $10^7$ beads. The antibodies were bound to the beads by incubating for 2 hours at 4° C. with gentle mixing using a mixing device from Tamiya. Afterwards, the tube containing the antibody-complexed beads were placed in the magnetic block and washed twice with washing buffer. For each wash the beads were gently resuspended in the washing buffer and then concentrated using the magnetic block. The beads were resuspended in 25 $\mu$l of washing buffer.

*Campylobacter jejuni* laboratory strain cj43429 was grown on Mueller-Hinton agar supplemented with defibrinated sheep blood as in Example 1. The Campylobacter was serial diluted in 10-fold increments in sterile water. Each sample was mixed with the anti-body coated beads in a tube and incubated for 1 hour at 4° C. on the mixing device. Then the tubes containing the samples were placed in the magnetic block to concentrate the beads and the supernatant fraction was removed. The beads were washed twice in washing buffer as above and then resuspended in sterile water. Determination of the number of cells remaining in the supernatant fractions unbound after the immunoseparation of each dilution was done by plating serial 10-fold dilutions of the supernatant fractions. The results are shown in Table 2.

TABLE 2

*Campylobacter jejuni* Cell Isolation By Immunomagnetic Beads

| Tube # | Total Cells | Cells Bound by Beads | Cells Unbound | % Cells Bound |
|---|---|---|---|---|
| 1 | $10^9$ | $2 \times 10^8$ | $8 \times 10^8$ | 20 |
| 2 | $10^7$ | 0 | $1 \times 10^7$ | 0 |
| 3 | $10^6$ | $8 \times 10^5$ | $2 \times 10^5$ | 80 |
| 4 | $10^5$ | $9.4 \times 10^4$ | $6 \times 10^3$ | 94 |
| 5 | $10^4$ | $2 \times 10^3$ | $8 \times 10^3$ | 20 |
| 6 | $10^3$ | $9.7 \times 10^2$ | $3 \times 10^1$ | 97 |
| 7 | $10^2$ | $7 \times 10^1$ | $3 \times 10^1$ | 70 |
| 8 | $10^1$ | 0 | 0 | 0 |
| 9 | $10^0$ | 0 | 0 | 0 |

The results show that the beads can capture up to 97% of the cells from each of the serial dilution mixtures. No cells were captured in mixtures that contained less than 10 cells. The efficiency of capture improved as the ratio between the coated immunomagnetic beads and target cells was increased. The results demonstrate that immunomagnetic beads can be used to purify and concentrate *Campylobacter jejuni* directly from environmental samples.

EXAMPLE 5

This example shows that the immunomagnetic separation step enables detection by PCR of about 10 CFU/ml of *Campylobacter jejuni*.

Immunomagnetic beads were prepared as in Example 4. *Campylobacter jejuni* laboratory strain cj43429 was grown on Mueller-Hinton agar supplemented with defibrinated sheep blood as in Example 1. The *Campylobacter jejuni* was serial diluted in 10-fold increments in sterile water. Cell isolations using the antibody complexed beads were performed on these dilutions as in Example 4. A set of 50 $\mu$l PCR reactions with 30 $\mu$l reagent and 20 1 sample were performed directly on the cells in each cell dilution. DNA was not isolated from the cells prior to the PCR reaction.

The final concentration of the components of the PCR mixture was 20 $\mu$l of the cell dilution, 1.5 mM PCR buffer (Perkin-Elmer), 1.5 mM $MgCl_2$, 0.5 pmole/$\mu$l JL 238, 0.5 pmole/$\mu$l JL 239, 0.8 mM each adenosine triphosphate, guanosine triphosphate, cytosine triphosphate, and thymidine triphosphate, or analogue thereof, 0.05 unit/$\mu$l of Taq polymerase (AMPLITAQ, Perkin Elmer # N801-00660), and water to bring the reaction volume to 50 $\mu$l. The PCR reaction was performed as follows: 95° C. for 10 minutes; then, 39 cycles wherein each cycle was 95° C. for 1 minute followed by 60° C. for 1 minute; then, 72° C. for 10 minutes; and finally, chilling the sample to 4° C. One PCR reaction contained *Campylobacter jejuni* laboratory strain cj43429 DNA as a positive control. The PCR product was resolved on agarose gels. The agarose gels were 2% agarose gels in 1× Tris-Borate-EDTA (TBE) buffer using Agarose from GIBCO (#15510-019) and containing 0.5 $\mu$g/ml ethidium bromide. 20 $\mu$l of each PCR sample was loaded per well. The gels were usually run at 80 volts and 150 milliamps for about an hour and a half. Afterwards, the DNA bands were visualized under ultraviolet light in an Alphaimage 2000.

Figure 10:
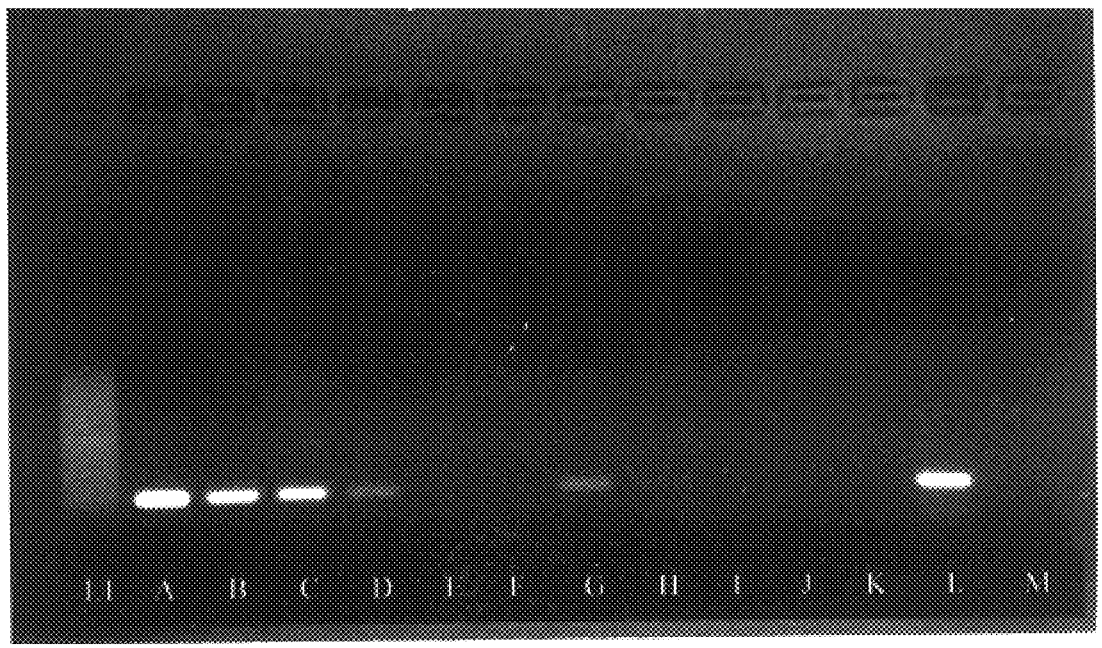
FIG. 10 shows an agarose gel stained with ethidium bromide of PCR products from cells isolated by immuno-magnetic separation of sterile water spiked with $10^9$ to $10^2$ CFU/ml of *Campylobacter jejuni* cj43429 (lanes A–G).

FIG. 10 shows that the immunomagnetic beads enabled detection by PCR of *Campylobacter jejuni* in a water sample that contained between 100 and 10 CFU/ml. In FIG. 10, the agarose gel shows the amplified PCR product from a *Campylobacter jejuni* sample containing either $10^9$ CFU/ml (lane A), $10^7$ CFU/ml (lane B), $10^6$ CFU/ml (lane C), $10^5$ CFU/ml (lane D), $10^4$ CFU/ml (lane E), $10^3$ CFU/ml (lane F), $10^2$ CFU/ml (lane G), or $10^1$ CFU/ml (lane H). Lane I contained the immunomagnetic beads only, J contained *Campylobacter jejuni* only (no beads), K contained PBS/1% BSA, and L1 contained *Campylobacter jejuni* DNA. Lane L1 contained a 100 bp DNA marker ladder and lane M contains a negative control consisting of a sterile water sample.

EXAMPLE 6

This example demonstrates the specificity of the immunomagnetic separation method for enabling PCR detection of *Campylobacter jejuni* from a mixture of *Campylobacter jejuni* and *Campylobacter coli*.

Immunomagnetic beads were prepared as in Example 4. *Campylobacter jejuni* laboratory strain cj43429 and *Campylobacter coli* strain cc1777208 were grown on Mueller-Hinton agar supplemented with defibrinated sheep blood as in Example 1. The Campylobacter species were mixed and the cells isolated as in Example 4. A set of 50 μl PCR reactions with 30 μl reagent and 20 μl sample were performed as in Example 5. DNA was not isolated from the samples prior to the PCR reaction. *Campylobacter jejuni* laboratory strain cj43429 DNA was used as a positive control. The PCR product was visualized by agarose gel electrophoresis followed by staining with ethidium bromide.

Figure 11:
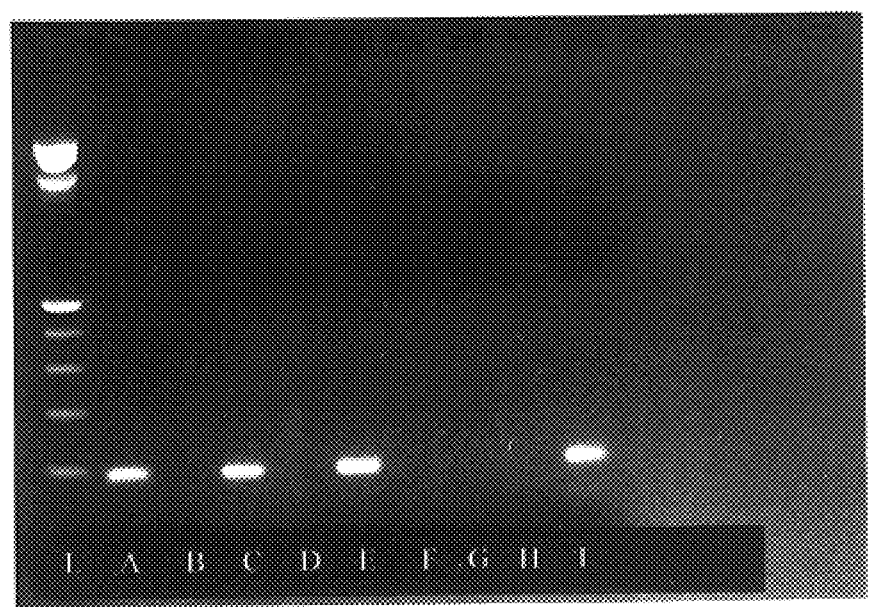
FIG. 11 shows an agarose gel stained with ethidium bromide of PCR products from cells isolated by immuno-magnetic separation of water samples spiked with *Campy-* lobacter jejuni cj43429 (lane A), Campylobacter coli cc1777208 (lane B), or both (lane C).

FIG. 11 shows that the PCR reaction following concentration with immunomagnetic beads is specific for *Campylobacter jejuni*. In FIG. 11, lane L is the DNA molecular weight markers, lane A shows the PCR product from a *Campylobacter jejuni* cell sample, lane B shows no PCR product from a *Campylobacter coli* cell sample, Lane D shows the PCR product from a mixture of cells from both, lane E shows no PCR product from PBS, Lane E shows the PCR product from a *Campylobacter jejuni* cell control, lane F shows no PCR product from a *Campylobacter coli* cell control, lane G shows no PCR product from uncoated beads that had been mixed with *Campylobacter jejuni*, lane H shows no PCR product from water, and Lane I shows the PCR product from *Campylobacter jejuni* DNA. The method is specific for *Campylobacter jejuni* because it did not detect *Campylobacter coli*. Furthermore, *Campylobacter coli* when mixed with *Campylobacter jejuni* did not interfere with recovery and detection of *Campylobacter jejuni*. Beads not coated with antibody did not capture *Campylobacter jejuni* indicating that the antibody is necessary for capture.

EXAMPLE 7

This example demonstrates the specificity of the immunomagnetic separation method for enabling PCR detection of *Campylobacter jejuni* from a mixture of *Campylobacter jejuni* and *Campylobacter coli* in fecal samples.

Immunomagnetic beads were prepared as in Example 4. *Campylobacter jejuni* laboratory strain cj43429 and *Campylobacter coli* strain cc1777208 were grown on Mueller-Hinton agar supplemented with defibrinated sheep blood as in Example 1. The Campylobacter was serial diluted in 10-fold increments in sterile water. Calf fecal samples were spiked with serial dilutions of *Campylobacter jejuni* alone and with a constant dilution of *Campylobacter coli*. Cell isolations using the antibody complexed beads were performed on these dilutions as in Example 4. A set of 50 μl PCR reactions with 30 μl reagent and 20 μl sample were performed as in Example 5. DNA was not isolated from the samples prior to the PCR reaction. *Campylobacter jejuni* laboratory strain cj43429 DNA was used as a positive control. The PCR product was visualized by agarose gel electrophoresis followed by staining with ethidium bromide.

FIG. 12 shows that the method detected $10^9$ *Campylobacter jejuni* in a mixture with $10^8$ *Campylobacter coli* in fecal samples. In FIG. 12, lane L is a DNA molecular weight ladder, lane A shows the PCR product from *Campylobacter jejuni* cells isolated from a mixture of $10^9$ cells in water using immunomagnetic beads, lane B shows the PCR product from *Campylobacter jejuni* cells isolated from a fecal mixture containing $10^9$ *Campylobacter jejuni* cells and $10^8$ *Campylobacter coli* cells using immunomagnetic beads, lane C shows no PCR product from *Campylobacter jejuni* cells isolated from a fecal mixture containing $10^7$ *Campylobacter jejuni* cells and $10^8$ *Campylobacter coli* cells using immunomagnetic beads, lane D shows no PCR product from *Campylobacter jejuni* cells isolated from a fecal mixture containing $10^6$ *Campylobacter jejuni* cells and $10^8$ *Campylobacter coli* cells using immunomagnetic beads, Lane E shows no PCR product for a sample isolated from a fecal mixture containing *Campylobacter coli* using immunomagnetic beads, Lane F shows no PCR product for a sample from a mixture of $10^9$ *Campylobacter jejuni* cells, lane G shows no PCR product from *Campylobacter jejuni* cells in a fecal mixture containing $10^9$ *Campylobacter jejuni* cells and $10^8$ *Campylobacter coli* cells, lane H shows no PCR product from *Campylobacter jejuni* cells in a fecal mixture containing $10^7$ *Campylobacter jejuni* cells and $10^8$ *Campylobacter coli* cells, lane I shows no PCR product from *Campylobacter jejuni* cells in a fecal mixture containing $10^6$ *Campylobacter jejuni* cells and $10^5$ *Campylobacter coli* cells, lane J shows no PCR product from a fecal mixture containing no Campylobacter spp., lane K shows no PCR product from a sample containing $10^5$ *Campylobacter jejuni* cells, lane K shows the PCR product from DNA isolated from *Campylobacter jejuni* cells, and M shows no PCR product for water. The results show that for detecting *Campylobacter jejuni* in fecal samples, the isolation parameters are to be modified to eliminate the contaminants in feces which is known to inhibit PCR reactions.

EXAMPLE 8

The example shows the PCR reaction detecting as few as 200 *Campylobacter jejuni* cells in a sample to as many as 200,000 cells in a sample.

Serial dilutions were made of *Campylobacter jejuni* cj43429 cells and subjected to PCR reactions as described in Example 5 and the PCR products analyzed on 2% agarose gels as described in Example 5.

The results are shown in FIG. 13. FIG. 13 shows in lane A the PCR product from *Campylobacter jejuni* DNA, and in lanes B, C, D, E, and F the PCR product from $10^9$, $10^7$, $10^6$, $10^5$, and $10^6$ *Campylobacter jejuni* cells. Lane L shows a DNA molecular weight ladder and lane G shows no PCR product for sterile water. Because only 20 μl of sample was used in the PCR reaction, each number (CFU/ml) is divided by 50 to determine the number of cells detected.

EXAMPLE 9

This example shows that the TAQMAN assay of the present invention to detect as few as 200 *Campylobacter jejuni* cells after 21 cycles.

The TAQMAN PCR reaction mixture concentrations were as follows: 1× TAQMAN buffer (available from Perkin-Elmer Applied Biosystems, Foster City, Calif.), 0.8 mM each DNTP, 0.5 pmole per μl each primer, 200 ηM TAQ1, 0.05 units per μl AMPLITAQ Gold polymerase (Perkin-Elmer Applied Biosystems), 0.01 units per μl AMPERASE UNG (Perkin-Elmer Applied Biosystems), 4.5 mM $MgCl_2$, 0.05% gelatin, and 0.01% TWEEN 20.

After an initial denaturation step at 95° C. for 10 minutes, the following cycle was repeated 40 times: 60° C. for 1 minute, followed by 95° C. for 30 seconds. Prior to the initial denaturation, all TAQMAN reactions were incubated at 50° C. for two minutes in the presence of AMPERASE UNG in an effort to prevent PCR product carryover. Detection of fluorescence emissions were monitored in real-time with an ABI Prism 7700 Sequence Detection System (Perkin-Elmer Applied Biosystems). DNA standards were prepared using *Campylobacter jejuni* chromosomal DNA serially diluted in reverse osmosis deionized water. The Passive Reference Dye used for normalization of reporter fluor signal was included in the TAQMAN reaction buffer. The results were reported as ΔRn vs. PCR cycle, wherein ΔRn is the difference in normalized reporter fluor signal between a PCR tube with sample DNA and a no DNA control. The threshold level (defined in ΔRn units), which is used to indicate a positive reaction, was adjusted to enhance the linear relationship between DNA mass and threshold cycle.

The results shown in FIG. 14 show that the TAQMAN assay can detect at least 200 *Campylobacter jejuni* cells after 21 cycles. The signal exceeded the signal from purified genomic DNA by cycle 32. In FIG. 14, A and B are negative controls, C and D are positive controls using 10 ηg of *Campylobacter DNA from cj43429*, and E and F are 200 cells of *Campylobacter jejuni*.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A process for detecting and enumerating *Campylobacter jejuni* in a sample, the process comprising:

(a) providing in a PCR reaction mixture a sample suspected to contain a target nucleic acid sequence that comprises QRDR region of the *Campylobacter jejuni* gyrA gene, a first oligonucleotide PCR primer comprising SEQ ID NO:3, and a second oligonucleotide PCR primer comprising SEQ ID NO:4, which hybridize to opposite strands of the target nucleic acid sequence and flank the target nucleic acid sequence for PCR amplification of the target nucleic acid sequence, each of four deoxynucleoside triphosphates selected from the group consisting of adenosine, guanosine, thymidine, cytosine, and analogs thereof, a nucleic acid polymerase having a 5' to 3' exonuclease activity and lacking 3' to 5' exonuclease activity, and an oligonucleotide probe comprising SEQ ID NO:5 blocked against chain extension at its 3' end and labeled at its 5' end with an energy transfer donor fluorophore and labeled at its 3' end with an energy transfer acceptor fluorophore wherein the oligonucleotide probe is complementary to the target nucleic acid;

(b) amplifying the target nucleic sequence in the sample under suitable PCR reaction mixture temperature conditions by a repetitive series of PCR thermal cycling steps comprising:

(1) denaturing the target nucleic acid sequence into opposite strands;

(2) hybridizing the first and second oligonucleotide PCR primers and the oligonucleotide probe to the denatured strands, and (3) extending the hybridized primers with the four deoxynucleoside triphosphates and the nucleic acid polymerase, and releasing the 5' energy transfer donor fluorophore and the 3' energy transfer acceptor fluorophore during the extension phase by the 5' to 3' exonuclease activity of the nucleic acid polymerase on the oligonucleotide probe annealed to the denatured strands;

(c) following amplification of the target nucleic acid sequence by one or more series of the thermal cycling steps, spectrophotometrically detecting and measuring the amount of fluorescence of the 5' energy transfer donor fluorophore released from the oligonucleotide probe wherein the fluorescence indicates the sample contains the *Campylobacter jejuni* and wherein the amount of fluorescence is proportional to the number of *Campylobacter jejuni* in the sample.

2. The process of claim 1 wherein the target nucleic acid sequence is the nucleotide sequence in SEQ ID NO:10.

3. The process of claim 1 wherein the fluorophore is selected from the group consisting of fluorescein, 5-carboxyfluorescein (FAM), 2'7'-dimethoxy-4',5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), tetrachloro-6-carboxy-fluorescein (TET), VIC, and 5-(2'-aminoethyl)aminonaphthalene-1-sulfonic acid (EDANS).

4. The process of claim 1 wherein the sample comprises a culture wherein an environmental sample containing the *Campylobacter jejuni* has been incubated to increase the amount of the *Campylobacter jejuni*.

5. The process of claim 1 wherein the sample comprises the *Campylobacter jejuni* which is isolated from an environmental sample by immunomagnetic separation.

6. A process for detecting in a sample antibiotic-resistant *Campylobacter jejuni* and wild-type *Campylobacter jejuni*, the process comprising:

(a) providing in a PCR reaction mixture a sample suspected to contain a target nucleic acid sequence that comprises QRDR region of the *Campylobacter jejuni* gyrA gene, a first oligonucleotide PCR primer comprising SEQ ID NO:3 and a second oligonucleotide PCR primer comprising SEQ ID NO:4, which hybridize to opposite strands of the target nucleic acid sequence and flank the target nucleic acid sequence for PCR amplification of the target nucleic acid sequence, each of four deoxynucleoside triphosphates selected from the group consisting of adenosine, guanosine, thymidine, cytosine, and analogs thereof, a nucleic acid polymerase having a 5' to 3' exonuclease activity and lacking 3' to 5' exonuclease activity, a first oligonucleotide probe comprising SEQ ID NO:6 blocked against chain extension at its 3' end and labeled at its 5' end with a first energy transfer donor fluorophore and labeled at its 3' end with an energy transfer acceptor fluorophore, and a second oligonucleotide probe comprising SEQ ID NO:7 blocked against chain extension at its 3' end and labeled at its 5' end with a second energy transfer donor fluorophore and labeled at its 3' end with an energy transfer acceptor fluorophore, wherein the first donor fluorophore emits fluorescent light of a different wavelength than the second donor fluorophore when released from the oligonucleotide probe, and wherein the first oligonucleotide probe is complementary to the sequence comprising the threonine-86 codon of the gyrA gene in the target nucleic acid from the wild-type *Campylobacter jejuni* and the second oligonucleotide probe is complementary to the sequence comprising the isoleucine-86 codon of the gyrA gene in the target nucleic acid from the antibiotic-resistant *Campylobacter jejuni;*

(b) amplifying the target nucleic sequence in the sample under suitable PCR reaction mixture temperature conditions by a repetitive series of PCR thermal cycling steps comprising:
   (1) denaturing the target nucleic acid sequence into opposite strands;
   (2) hybridizing the first and second oligonucleotide PCR primers and the first and second oligonucleotide probes to the denatured strands, and
   (3) extending the hybridized primers with the four deoxynucleoside triphosphates and the nucleic acid polymerase, and releasing the 5' energy transfer donor fluorophore and the 3' energy transfer acceptor fluorophore during the extension phase by the 5' to 3' exonuclease activity of the nucleic acid polymerase on the oligonucleotide probe annealed to the denatured strands;

(c) following amplification of the target nucleic acid sequence by one or more series of the thermal cycling steps, spectrophotometrically detecting and measuring an amount of fluorescence of the 5' energy transfer donor fluorophore released from the oligonucleotide probe wherein fluorescence of the first 5' energy transfer donor fluorophore indicates the sample contains wild-type *Campylobacter jejuni* and fluorescence of the second 5' energy transfer donor fluorophore indicates the sample contains antibiotic-resistant *Campylobacter jejuni* and wherein a ratio of the first and second fluorescence is proportional to the ratio of the wild-type and the antibiotic-resistant *Campylobacter jejuni* in the sample.

7. The process of claim 6 wherein the target nucleic acid sequence is the nucleotide sequence in SEQ ID NO:10.

8. The process of claim 6 wherein the fluorophore is selected from the group consisting of fluorescein, 5-carboxyfluorescein (FAM), 2'7'-dimethoxy-4',5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), tetrachloro-6-carboxy-fluorescein (TET), VIC, and 5-(2'-aminoethyl)aminonaphthalene-1-sulfonic acid (EDANS).

9. The process of claim 6 wherein the antibiotic-resistant *Campylobacter jejuni* is resistant to ciprofloxacin.

10. The process of claim 6 wherein the sample comprises a culture wherein an environmental sample containing the *Campylobacter jejuni* has been incubated to increase the amount of the Campylobacter jejuni.

11. The process of claim 6 wherein the sample comprises a culture from which an environmental sample containing the *Campylobacter jejuni* is cultivated.

12. A kit for detecting *Campylobacter jejuni* in a sample comprising in one or more containers:

(a) a first oligonucleotide primer consisting of SEQ ID NO:3;

(b) a second oligonucleotide primer consisting of SEQ ID NO:4; and (c) an oligonucleotide probe consisting of SEQ ID NO:5, which is blocked against chain extension at its 3' end and labeled at its 5' end with an energy transfer donor fluorophore and labeled at its 3' end with an energy transfer acceptor fluorophore, wherein the first and second oligonucleotide primers hybridize to opposite strands of a target sequence comprising the QRDR region of the *Campylobacter jejuni* gyrA gene and flank the target nucleic acid sequence for PCR amplification of the target nucleic acid sequence and wherein the oligonucleotide probe is complementary to a sequence within the target nucleic acid sequence and wherein the oligonucleotide probe enables fluorescence detection and enumeration of the *Campylobacter jejuni.*

13. The kit of claim 12 wherein the fluorophore is selected from the group consisting of fluorescein, 5-carboxyfluorescein (FAM), 2'7'-dimethoxy-4',5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), tetrachloro-6-carboxy-fluorescein (TET), VIC, and 5- (2'-aminoethyl)aminonaphthalene-1-sulfonic acid (EDANS).

14. A kit for detecting antibiotic-resistant and wild-type *Campylobacter jejuni* in a sample comprising in one or more containers:

(a) a first oligonucleotide primer comprising SEQ ID NO:3;

(b) a second oligonucleotide primer comprising SEQ ID NO:4;

(c) a first oligonucleotide probe comprising SEQ ID NO:6; and (d) a second oligonucleotide probe comprising SEQ ID NO:7, wherein the first and second oligonucleotide primers are specific for QRDR region of the *Campylobacter jejuni* gyrA gene and hybridize to opposite strands of a target sequence comprising the QRDR and flank the target nucleic acid sequence for PCR amplification of the target nucleic acid sequence, wherein the first and second oligonucleotide probes are blocked against chain extension at its 3' end and labeled at the 5' end with a an energy transfer donor fluorophore and labeled at the 3' end with an energy transfer acceptor fluorophore, wherein the donor fluorophore on the first oligonucleotide probe emits fluorescent light of a different wavelength than the donor fluorophore on the second oligonucleotide probe when released from the oligonucleotide probe, and wherein the first oligonucleotide probe is complementary to a sequence comprising the threonine-86 codon of the QRDR from the wild-type *Campylobacter jejuni* and the second oligonucleotide probe is complementary sequence comprising the isoleucine-86 codon of the QRDR from the antibiotic-resistant *Campylobacter jejuni.*

15. The kit of claim 14 wherein the fluorophore is selected from the group consisting of fluorescein, 5-carboxyfluorescein (FAM), 2'7'-dimethoxy-4',5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), tetrachloro-6-carboxy-fluorescein (TET), VIC, and 5-(2'-aminoethyl)aminonaphthalene-1-sulfonic acid (EDANS).

16. The kit of claim 14 wherein the antibiotic-resistant *Campylobacter jejuni* is resistant to ciprofloxacin.

17. A labeled nucleic acid probe for detecting *Campylobacter jejuni* DNA consisting of the nucleotide sequence 5'-TTTGCTTCAGTATAACGCATCGCAGC-3' (SEQ ID NO:5).

18. The probe of claim 17 wherein the probe is labeled at its 5' end with an energy transfer donor fluorophore and labeled at its 3' end with an energy transfer acceptor fluorophore.

19. The probe of claim 18 wherein the fluorophore is selected from the group consisting of fluorescein, 5-carboxyfluorescein (FAM), 2'7'-dimethoxy-4',5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), tetrachloro-6-carboxy-fluorescein (TET), VIC, and 5-(2'-aminoethyl)aminonaphthalene-1-sulfonic acid (EDANS).

20. The probe of claim 17 wherein the probe is blocked against chain extension at its 3' end.

21. A labeled nucleic acid probe for detecting *Campylobacter jejuni* DNA resistant to an antibiotic comprising the nucleotide sequence 5'-CCACATGGAGATATAGCAGTTTATGATGC-3' (SEQ ID NO:7).

22. The probe of claim 21 wherein the probe is labeled at its 5' end with an energy transfer donor fluorophore and labeled at its 3' end with an energy transfer acceptor fluorophore.

23. The probe of claim 22 wherein the fluorophore is selected from the group consisting of fluorescein, 5-carboxyfluorescein (FAM), 2'7'-dimethoxy-4',5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), tetrachloro-6-carboxy-fluorescein (TET), VIC, and 5-(2'-aminoethyl)aminonaphthalene-1-sulfonic acid (EDANS).

24. The probe of claim 21 wherein the probe is blocked against chain extension at its 3' end.

25. A process for detecting *Campylobacter jejuni* in a sample, the process comprising:
  (a) providing in a PCR reaction mixture a sample suspected to contain a target nucleic acid sequence that comprises QRDR of the *Campylobacter jejuni* gyrA gene, a first oligonucleotide PCR primer comprising SEQ ID NO:3 and a second oligonucleotide PCR primer comprising SEQ ID NO:4, which hybridize to opposite strands of the target nucleic acid sequence and flank the target nucleic acid sequence for PCR amplification of the target nucleic acid sequence, each of four deoxynucleoside triphosphates selected from the group consisting of adenosine, guanosine, thymidine, cytosine, and analogs thereof, and a nucleic acid polymerase having a 5' to 3' exonuclease activity and lacking 3' to 5' exonuclease activity;
  (b) amplifying the target nucleic sequence in the sample under suitable PCR reaction mixture temperature conditions to provide a detectable amount of amplified target nucleic acid sequence by a repetitive series of PCR thermal cycling steps comprising:
    (1) denaturing the target nucleic acid sequence into opposite strands;
    (2) hybridizing the first and second oligonucleotide PCR primers and the oligonucleotide probe to the denatured strands, and
    (3) extending the hybridized primers with the four deoxynucleoside triphosphates and the nucleic acid polymerase; and
  (c) detecting the amplified target nucleic acid sequence wherein the detection of the amplified target nucleic acid sequence is indicative of the presence of the *Campylobacter jejuni*.

26. The process of claim 25 wherein the target nucleic acid sequence is the nucleotide sequence in SEQ ID NO:10.

27. The process of claim 25 wherein the sample comprises a culture wherein an environmental sample containing the *Campylobacter jejuni* has been incubated to increase the amount of the *Campylobacter jejuni*.

28. The process of claim 25 wherein the sample comprises the *Campylobacter jejuni* which is isolated from an environmental sample by immunomagnetic separation.

29. The process of claim 25 wherein a labeled probe selected from the group consisting of SEQ ID NO:6 and SEQ ID NO:7 is hybridized to the amplified target nucleic acid sequence to determine whether the *Campylobacter jejuni* is antibiotic-resistant.

* * * * *

UNITED STATES PATENT AND TRADEMARK OFFICE
CERTIFICATE OF CORRECTION

PATENT NO. : 6,355,435 B1
DATED : March 12, 2002
INVENTOR(S) : David L. Wilson, John E. Linz, John B. Kaneene, Linda S. Mansfield, Robert D. Walker and Thomas C. Newman It is certified that error appears in the above-identified patent and that said Letters Patent is hereby corrected as shown below:

Column 4,
Line 15, "its 31 end" should be -- its 3' end --.

Column 5,
Line 53, "a" before "an energy" should be deleted.

Column 7,
Line 32, "Fig. 3 shows" should be -- Figs. 3 and 3B show --.

Figures 7A, 7B:
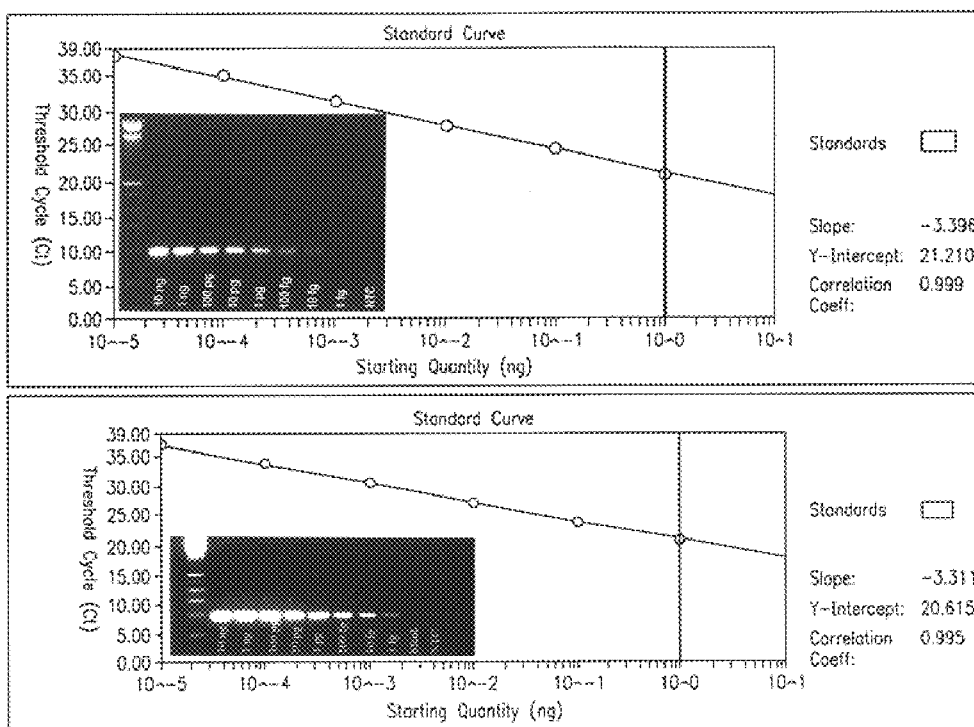
FIG. 7 shows standard curves of initial DNA mass in a reaction verses threshold cycle. Ten-fold serial dilutions of Campylobacter chromosomal DNA were performed and equal aliquots of each dilution were used in the reactions shown in FIG. 4. The starting quantity of DNA in these reactions is plotted verses the threshold cycle. (A) shows a standard curve derived from reactions using the TAQ2 probe. (B) shows the standard curve derived from reactions using the TAQ1 probe. The insets represent gel electrophoresis analysis of 20 µl of each of the 50 µl reactions. The left lane of the inserts show the 100 bp DNA markers.

Column 8,
Line 9, "Fig. 6 shows" should be -- Figs. 6A and 6B show --.
Line 27, "Fig. 7 shows" should be -- Figs. 7A and 7B show --.
Line 38, "Fig. 8 shows" should be -- Figs. 8A and 8B show --.
Line 49, "wild-typ" should be -- wild-type --.

Column 12,
Line 19, "$2x(\Sigma+T)+4x(\Sigma+C)$" should be -- $2x(\Sigma A+T)+4x(\Sigma G+C)$ --.

Column 13,
Line 8, "$5^{\circ}C$" should read -- $50^{\circ}C$ --.

Column 17,
Line 47, "$40^{\circ}C$" should read -- $4^{\circ}C$ --.
Table 1, line 1, "Aeromoras" should be -- Aeromonas --.
Table 1, (Column 4, line 3,) "1994" should be -- 1995 --.

Column 19,
Table 1, line 65, "33599" should be -- 33559 --.

Column 21,
Line 51, "each DNTP" should be -- dNTP --.

Column 24,
Line 23, "Figs 8 and 9" should be -- Figs 8A and 8B and 9 --.
Line 40, "In Fig. 8" should be -- In Figs. 8A and 8B --.
Line 60, "Fig. 3" should be -- Fig. 3A and 3B --.

Column 25,
Line 21, "*jejuni* but to also" should be -- *jejuni* but also --.

UNITED STATES PATENT AND TRADEMARK OFFICE
CERTIFICATE OF CORRECTION

PATENT NO. : 6,355,435 B1
DATED : March 12, 2002
INVENTOR(S) : David L. Wilson, John E. Linz, John B. Kaneene, Linda S. Mansfield, Robert D. Walker and Thomas C Newman It is certified that error appears in the above-identified patent and that said Letters Patent is hereby corrected as shown below:

Column 26,
Line 36, "20 l" should be -- 20$\mu$l --.

Column 27,
Line 1, "$^{101}$ CFU" should be -- $10^1$ CFU --.
Line 4, "L1 contained" should be -- L contained --.

Column 28,
Line 28, "and $10^5$" should be -- and $10^8$ --.
Line 63, "DNTP" should be -- dNTP --.

Column 40,
Line 1, should read as follows:

-- The process of Claim 6 wherein the sample comprises the
Campylobacter jejuni which is isolated from an
environmental sample by immunomagnetic separation --.

Signed and Sealed this

Eighth Day of October, 2002

Attest:

JAMES E. ROGAN
Attesting Officer    Director of the United States Patent and Trademark Office